(12) United States Patent
Nam et al.

(10) Patent No.: US 10,254,230 B2
(45) Date of Patent: Apr. 9, 2019

(54) NANOPARTICLES IN THE SHAPE OF NANOSNOWMAN WITH A HEAD PART AND A BODY PART, A PREPARATION METHOD THEREOF AND A DETECTION METHOD USING THE SAME

(71) Applicant: SEOUL NATIONAL UNIVERSITY R&DB FOUNDATION, Seoul (KR)

(72) Inventors: Jwa Min Nam, Seoul (KR); Jung Hoon Lee, Seoul (KR); Jeong Wook Oh, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 35 days.

(21) Appl. No.: 15/363,567

(22) Filed: Nov. 29, 2016

(65) Prior Publication Data

US 2017/0108440 A1    Apr. 20, 2017

Related U.S. Application Data

(62) Division of application No. 13/786,744, filed on Mar. 6, 2013, now abandoned.

(30) Foreign Application Priority Data

May 4, 2012    (KR) ........................ 10-2012-0047752

(51) Int. Cl.
*G01N 21/65* (2006.01)
*G01N 33/543* (2006.01)
*G01N 33/553* (2006.01)

(52) U.S. Cl.
CPC ..... *G01N 21/658* (2013.01); *G01N 33/54346* (2013.01); *G01N 33/553* (2013.01); *G01N 2021/653* (2013.01)

(58) Field of Classification Search
None
See application file for complete search history.

(56) References Cited

U.S. PATENT DOCUMENTS 5,306,403 A    4/1994    Vo-Dinh
6,022,471 A    2/2000    Wachter et al.
(Continued)

FOREIGN PATENT DOCUMENTS

KR    1020110066881 A    6/2011

OTHER PUBLICATIONS

Lee et al "Directional synthesis and assembly of bimetallic nanosnowment with DNA", JACS 2012, 134: Supplemental Infornnationnn, S1-S6 (Year: 2012).*

(Continued)

*Primary Examiner* — Betty J Forman
(74) *Attorney, Agent, or Firm* — Seed IP Law Group LLP

(57) ABSTRACT

The present invention relates to nanoparticles in the shape of nanosnowman with a head part and a body part, a preparation method thereof, and a detection method using the same. More particularly, the present invention relates to nanoparticles in the shape of nanosnowman with head and body parts, which can offer platforms for DNA-based assembly of various aligned and unconventional nanostructures and is highly applicable to the detection of DNA and an analyte associated, with the onset and progression of a particular disease, a preparation method thereof, and a detection method using the same.

12 Claims, 21 Drawing Sheets

Specification includes a Sequence Listing.

(56) References Cited

U.S. PATENT DOCUMENTS

| | | | |
|---|---|---|---|
| 6,040,191 | A | 3/2000 | Grow |
| 6,149,868 | A | 11/2000 | Natan et al. |
| 6,174,677 | B1 | 1/2001 | Vo-Dinh |
| 6,313,914 | B1 | 11/2001 | Roe |
| 2002/0146745 | A1 | 10/2002 | Natan et al. |
| 2002/0160195 | A1 | 10/2002 | Halas et al. |
| 2005/0101020 | A1 | 5/2005 | Salem et al. |
| 2008/0213189 | A1 | 9/2008 | Lee et al. |
| 2014/0113283 | A1* | 4/2014 | Suh .................. G01N 21/658 435/6.1 |

OTHER PUBLICATIONS

Caswell et al., "Preferential End-to-End Assembly of Gold Nanorods by Biotin—Streptavidin Connectors," *J. Am. Chem. Soc. 125*:13914-13915, 2003.

Chen et al., "Kinetics of Receptor Directed Assembly of Multisegment Nanowires," *J. Phys. Chem. B 110*:211-217, 2006.

Chen et al., "Preparation of Unique 1-D Nanoparticle Superstructures and Tailoring their Structural Features,"*J. Am. Chem. Soc. 132*:6902-6903, 2010.

Feldheim, "Assembly of Metal Nanoparticle Arrays Using Molecular Bridges," *The Electronic Society Interface*, Fall 2001, pp. 22-25.

Gole et al., "Biotin—Streptavidin-Induced Aggregation of Gold Nanorods. Tuning Rod—Rod Orientation," *Langmuir 21*:10756-10762, 2005.

Gu et al., "Facile One-Pot Synthesis of Bifunctional Heterodimers of Nanoparticles: A Conjugate of Quantum Dot and Magnetic Nanoparticles," *J. Am. Chem. Soc. 126*:5664-5665, 2004.

Gu et al., "Heterodimers of Nanoparticles: Formation at a Liquid—Liquid Interface and Particle-Specific Surface Modification by Functional Molecules," *J. Am. Chem. Soc. 127*:34-35, 2005.

Huang et al., "Room-Temperature Ultraviolet Nanowire Nanolasers," *Science 292*:1897-1899, 2001.

Hurst et al., "Maximizing DNA Loading on a Range of Gold Nanoparticle Sizes," *Anal. Chem. 78*(24):8313-8318, Dec. 15, 2006.

Kahraman et al., "Oligonucleotide-Mediated Au—Ag Core-Shell Nanoparticles," *Plasmonics 4*:293-301, 2009.

Lassiter et al., "Close Encounters between Two Nanoshells," *Nano Letters 8*(4):1212-1218, 2008.

Lee et al., "Directional Synthesis and Assembly of Biometallic Nanosnowmen with DNA," *Journal of the American Chemical Society 134*: 5456-5459, published Mar. 6, 2012.

Lim et al., "DNA-embedded Au/Ag core-shell nanoparticles," *Chem. Commun.*, pp. 5312-5314, 2008.

Lim et al., "Highly uniform and reproducible surface-enhanced Raman scattering from DNA-tailorable nanoparticles with 1-nm interior gap," *Nature Nanotechnology 6*:452-460, Jul. 2011.

Lim et al., "Nanogap-engineerable Raman-active nanodumbbells for single-molecule detection," *Nature Materials 9*:60-67, Jan. 2010.

Lu et al., "Asymmetric Dimers Can Be Formed by Dewetting Half-Shells of Gold Deposited on the Surfaces of Spherical Oxide Colloids," *J. Am. Chem. Soc. 125*:12724-12725, 2003.

Perro et al., "Design and synthesis of Janus micro- and nanoparticles," *J. Mater. Chem. 15*:3745-3760, 2005.

Sacanna et al., "Lock and key colloids," *Nature Letters 464*:575-578, Mar. 25, 2010.

Salant et al., "Directed Self-Assembly of Gold-Tipped CdSe Nanorods," *J. Am. Chem. Soc. 128*:10006-10007, 2006.

Salem et al., "Directed Assembly of Multisegment Au/Pt/Au Nanowires," *Nano Letters 4*(6):1163-1165, 2004.

Shi et al., "A General Approach to Binary and Ternary Hybrid Nanocrystals," *Nano Letters 6*(4):875-881, 2006.

Storhoff et al., "Sequence-Dependent Stability of DNA-Modified Gold Nanoparticles," *Langmuir 18*:6666-6670, 2002.

Tan et al., "Building plasmonic nanostructures with DNA," *Nature Nanotechnology 6*:268-276, May 2011.

Wiley et al., "Maneuvering the Surface Plasmon Resonance of Silver Nanostructures through Shape-Controlled Synthesis," *J. Phys. Chem. B 110*:15666-15675, 2006.

Wu et al., "Single-crystal metallic nanowires and metal/semiconductor nanowire heterostructures," *Nature 430*:61-65, Jul. 1, 2004.

Zhang et al., "PVP Protective Mechanism of Ultrafine Silver Powder Synthesized by Chemical Reduction Processes," *Journal of Solid State Chemistry 121*:105-110, 1996.

\* cited by examiner

FIG. 1A
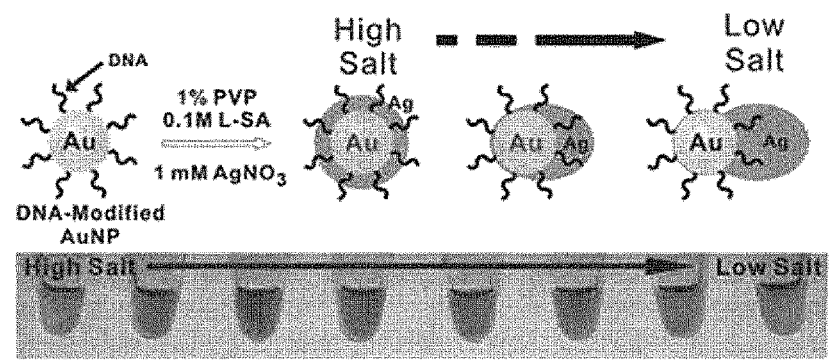
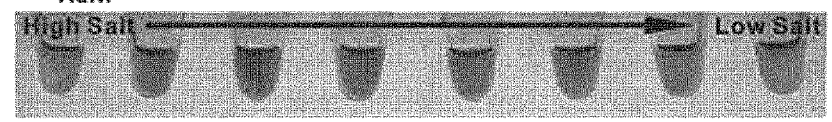
FIG. 1B
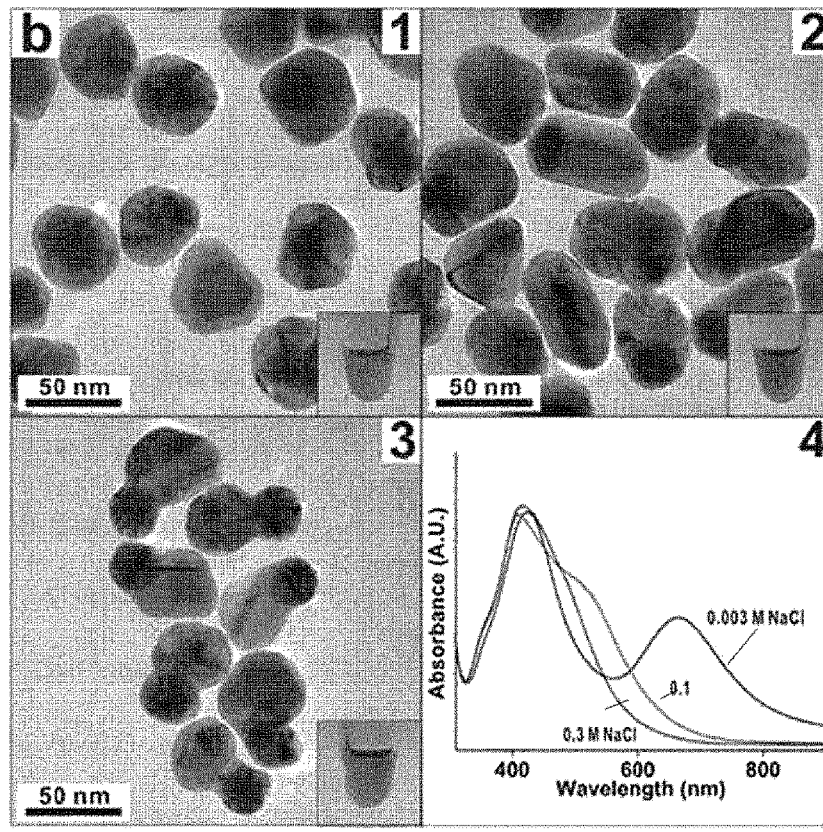

[FIG. 2]
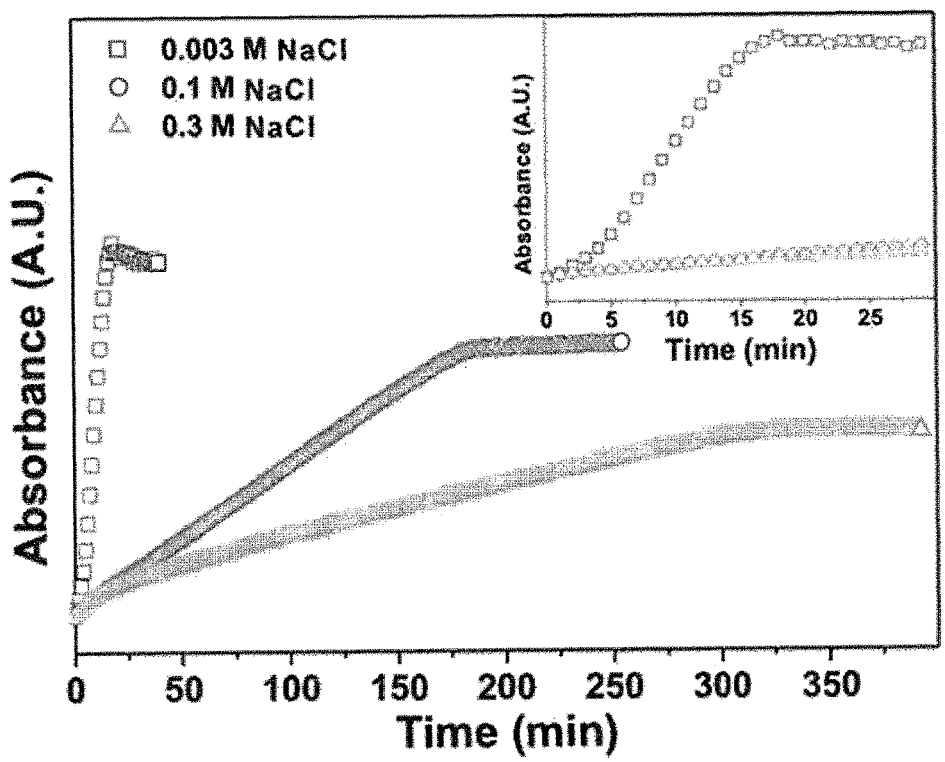

[FIG. 3]
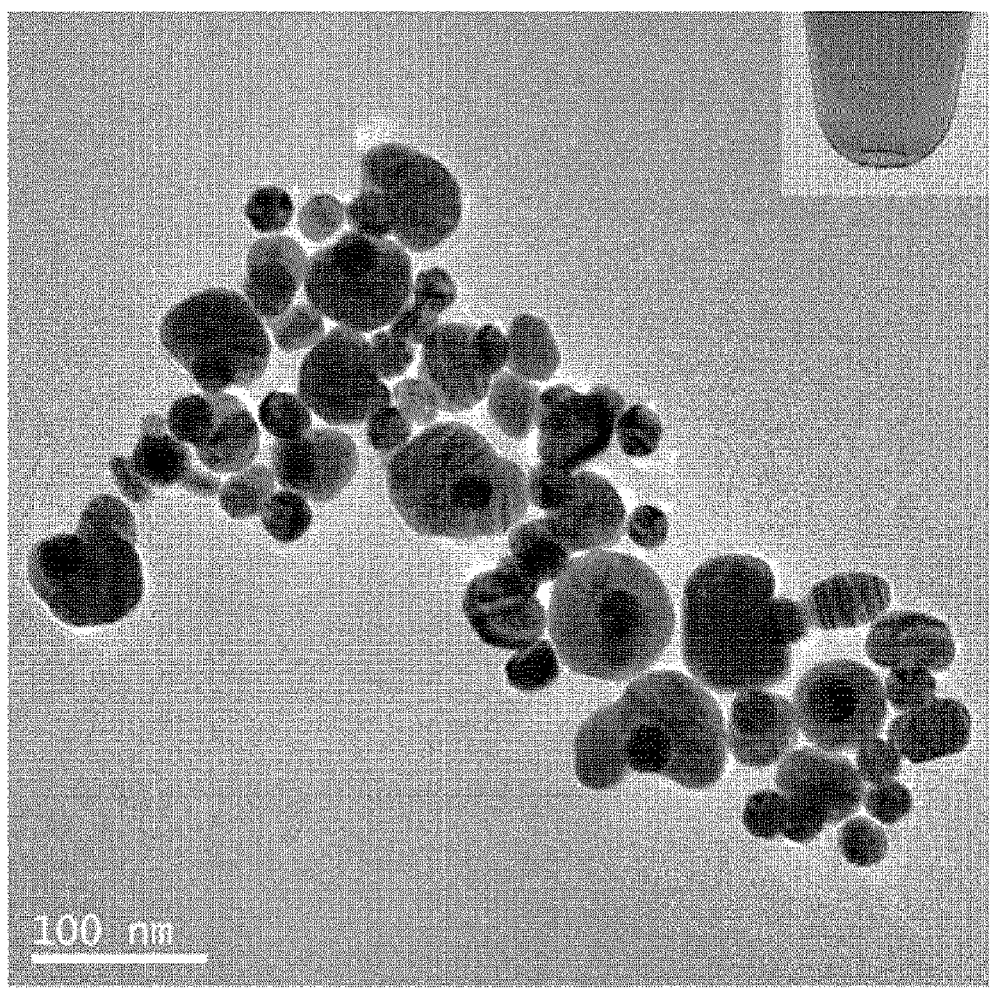

FIG. 4A
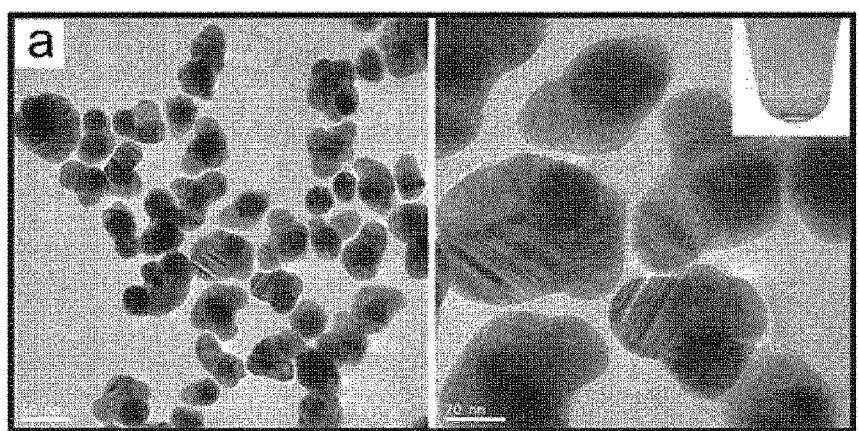
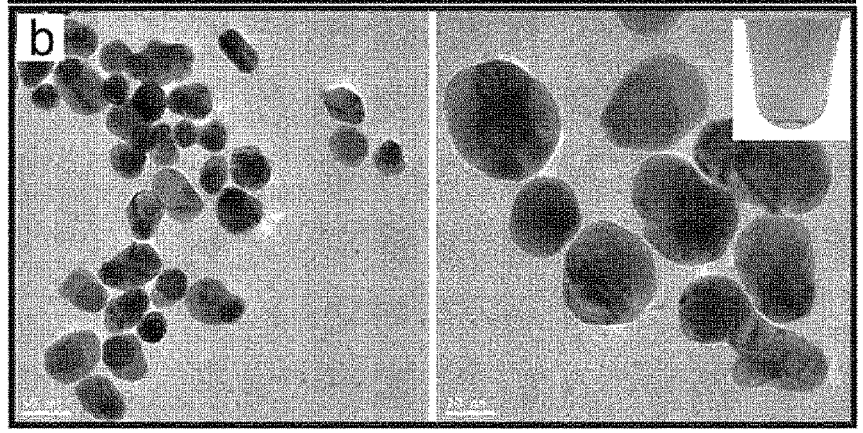
FIG. 4B

[FIG. 5]
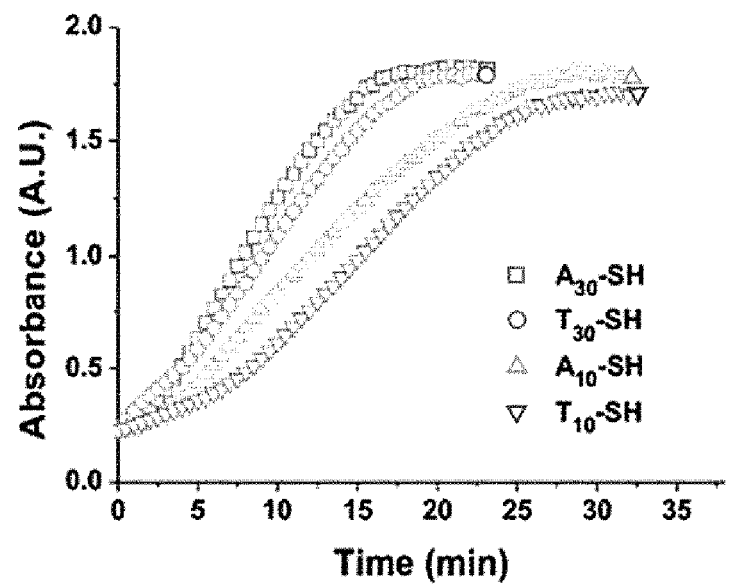
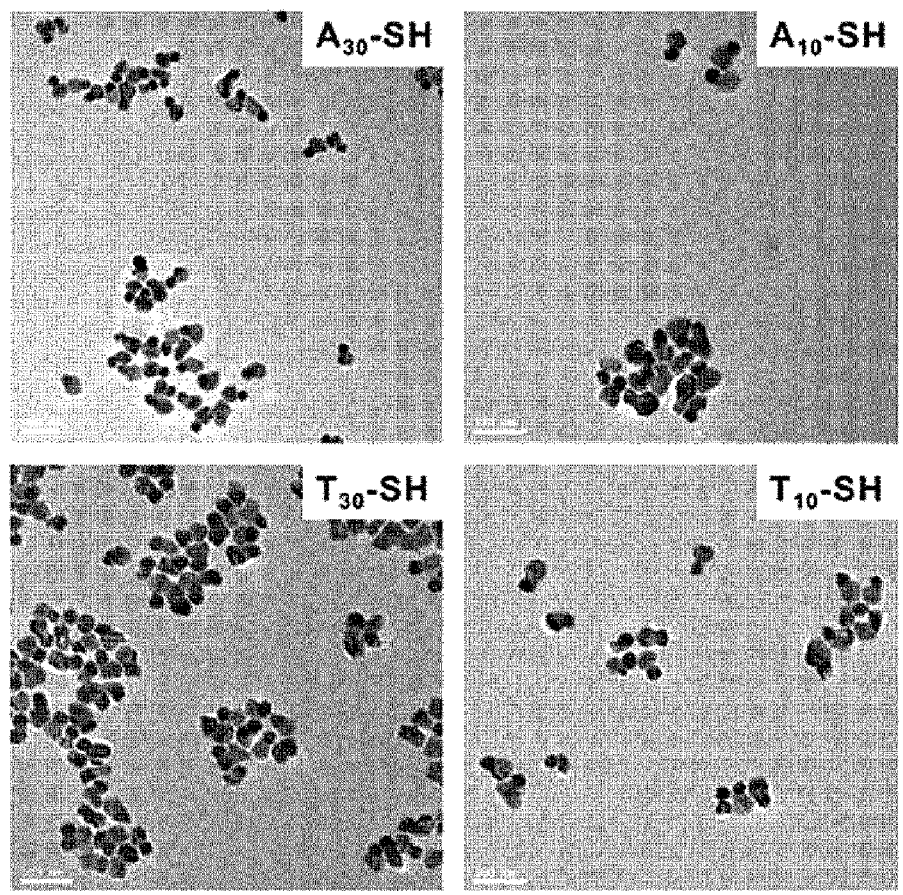

[FIG. 6]
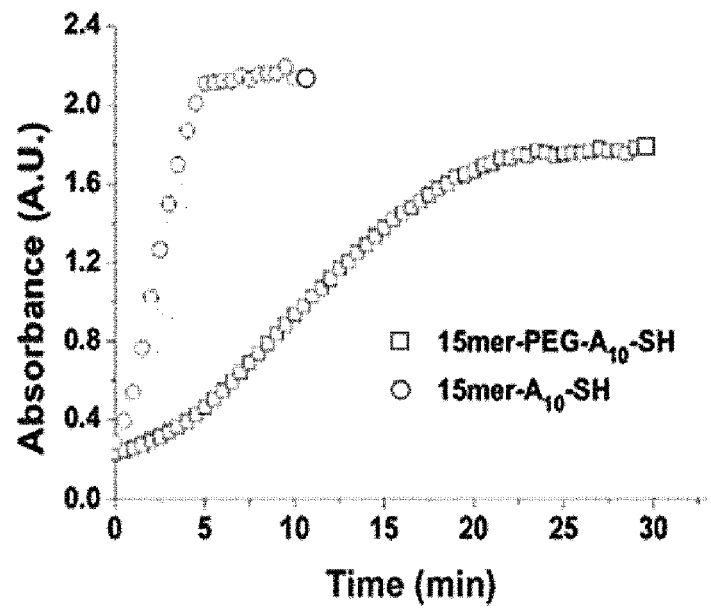
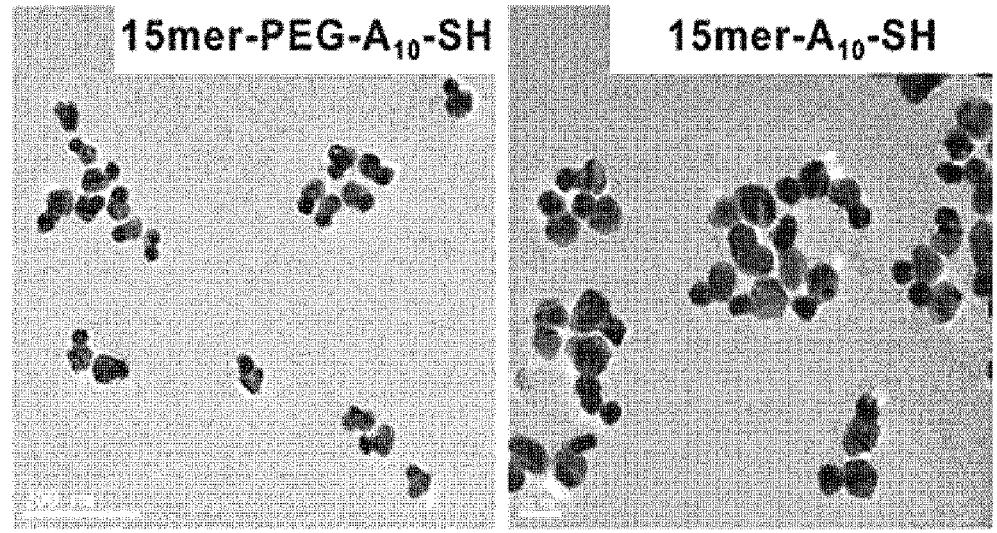

[FIG. 11]
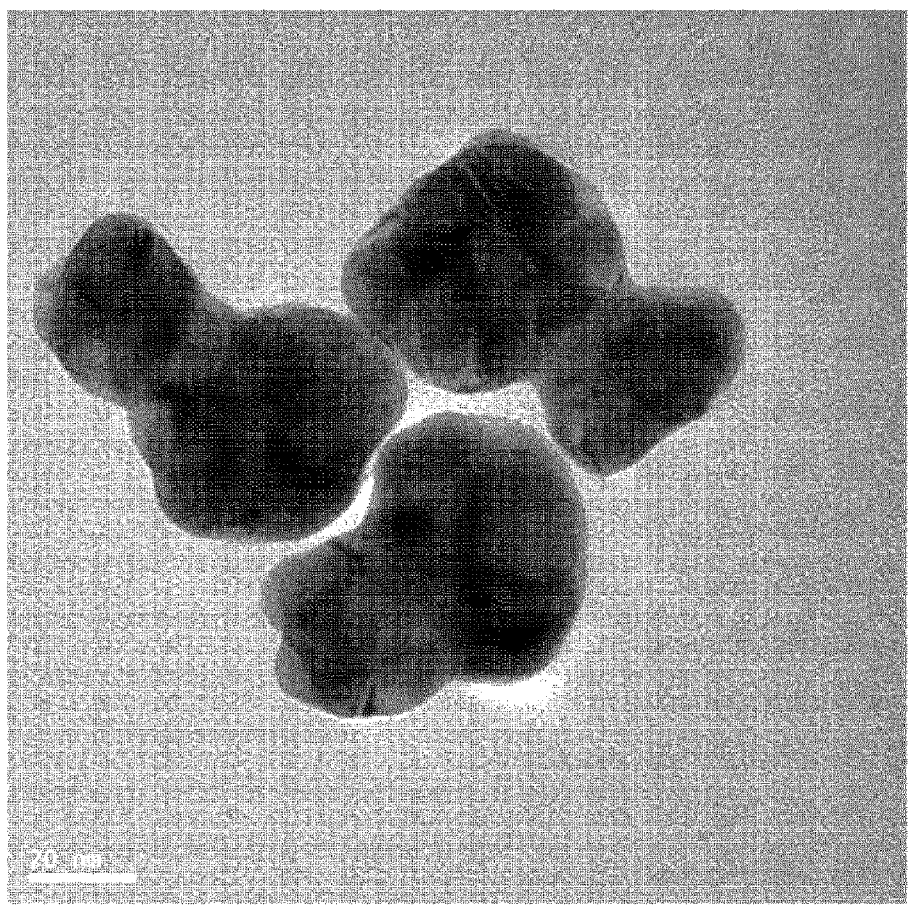

[FIG. 12]
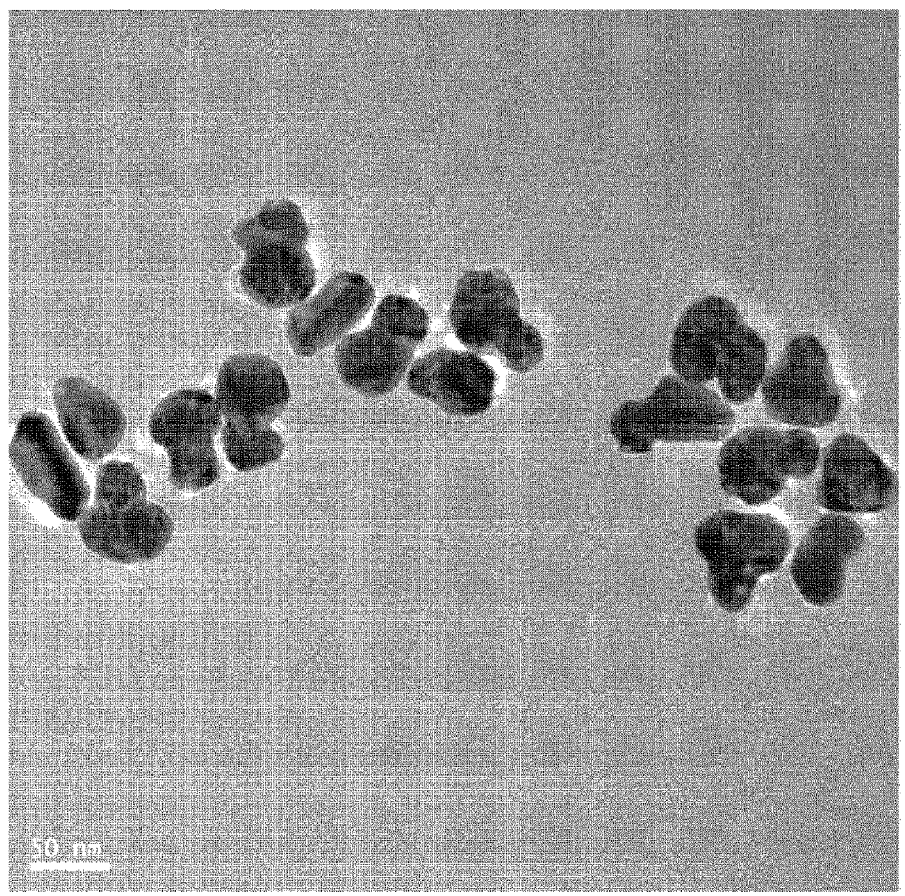

[FIG. 17]
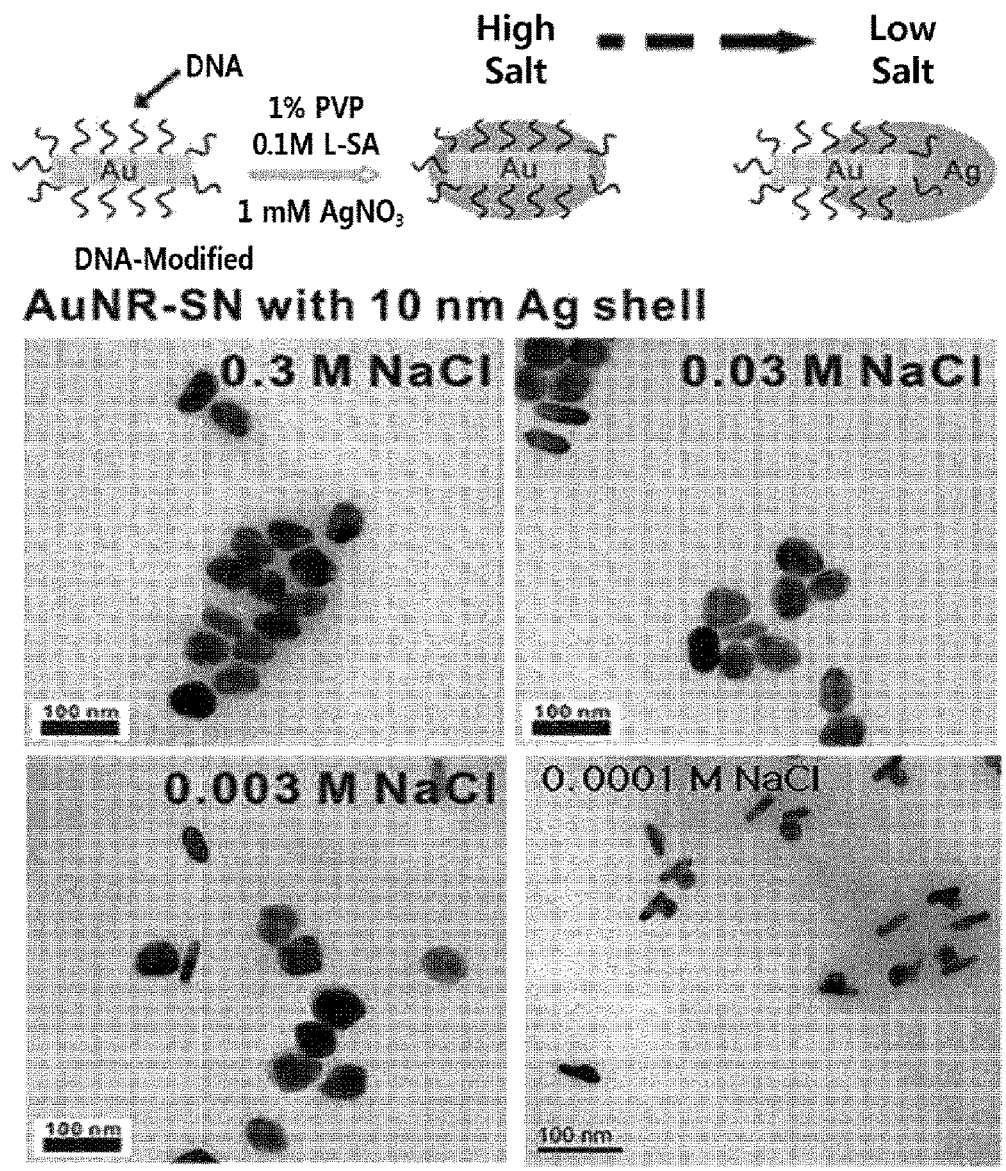

[FIG. 18]
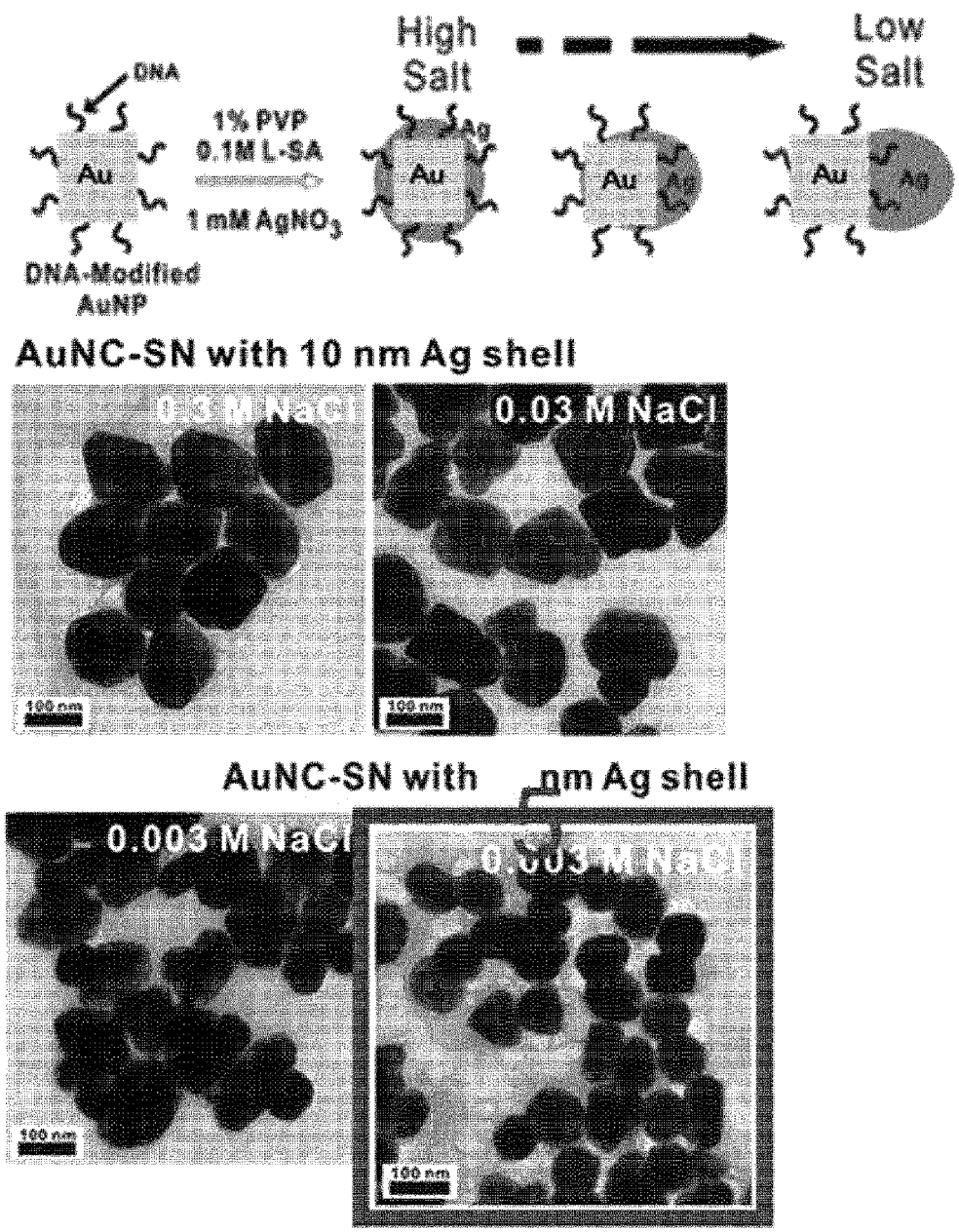

[FIG. 19]
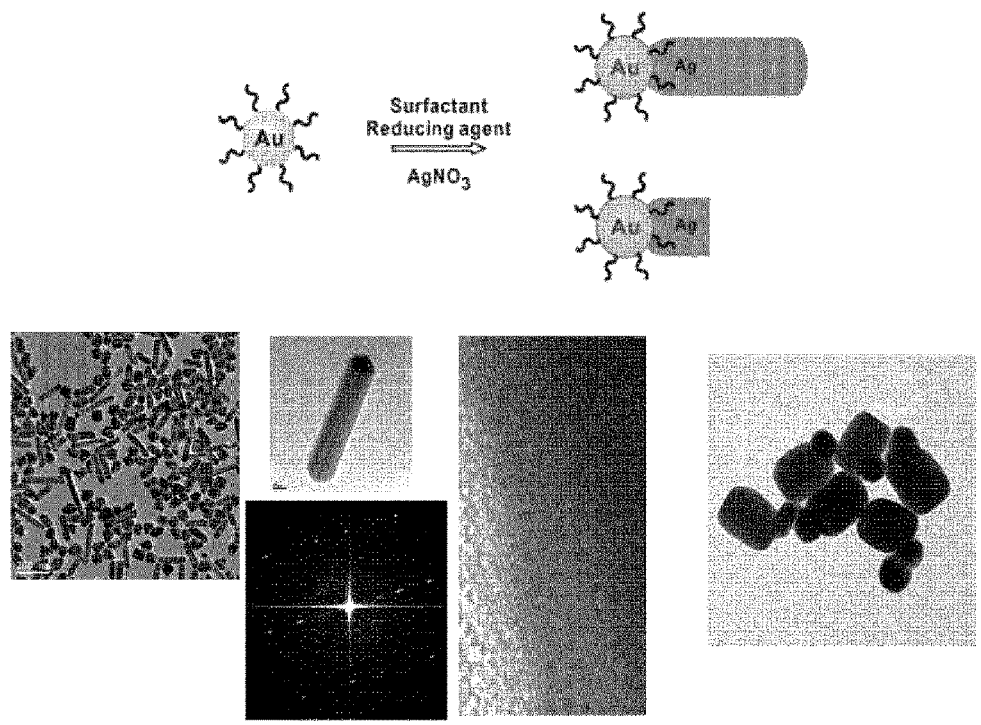
[FIG. 20]
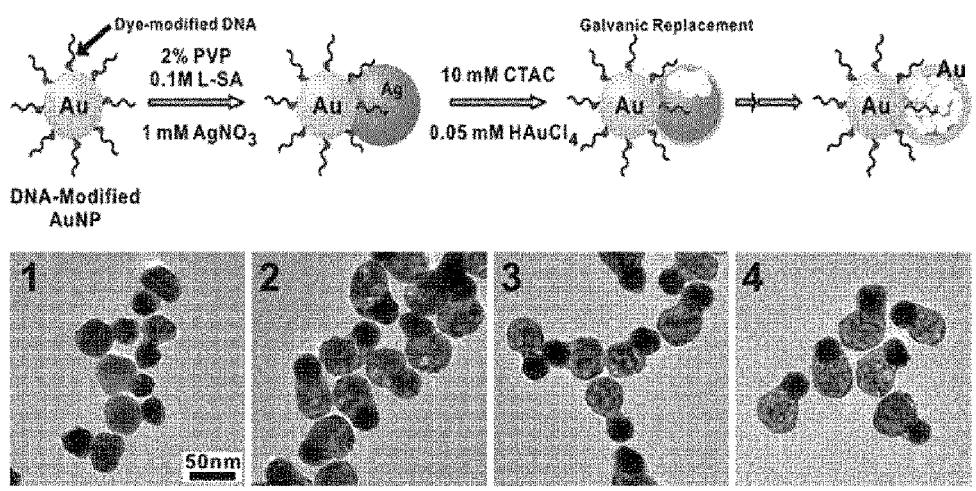

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: probe DNA

<400> SEQUENCE: 1
taacaataat ccctc                                                      15

<210> SEQ ID NO 2
<211> LENGTH: 15
```

```
<212> TYPE: DNA
<213> ORGANISM: Artificial Sequence
<220> FEATURE:
<223> OTHER INFORMATION: Probe DNA2

<400> SEQUENCE: 2
atccttatca atatt                                                    15

<210> SEQ ID NO 3
<211> LENGTH: 15
<212> TYPE: DNA
<213> ORGANISM: Artificial Sequence
<220> FEATURE:
<223> OTHER INFORMATION: Protecting DNA

<400> SEQUENCE: 3
cacgagtttc tcaaa                                                    15

<210> SEQ ID NO 4
<211> LENGTH: 30
<212> TYPE: DNA
<213> ORGANISM: Artificial Sequence
<220> FEATURE:
<223> OTHER INFORMATION: Linker DNA

<400> SEQUENCE: 4
gagggattat tgttaaatat tgataaggat                                    30
```

NANOPARTICLES IN THE SHAPE OF NANOSNOWMAN WITH A HEAD PART AND A BODY PART, A PREPARATION METHOD THEREOF AND A DETECTION METHOD USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 860175_404D1_SEQUENCE_LISTING.txt. The text file is 2 KB, was created on Nov. 29, 2016, and is being submitted electronically via EFS-Web.

BACKGROUND OF THE INVENTION

1. Field of the Invention

The present invention relates to nanoparticles in the shape of nanosnowman with a head part and a body part, a preparation method thereof, and a detection method using the same. More particularly, the present invention relates to nanoparticles in the shape of nanosnowman with head and body parts, which can offer platforms for DNA-based assembly of various aligned and unconventional nanostructures and is highly applicable to the detection of DNA and an analyte associated with the onset and progression of a particular disease, a preparation method thereof, and a detection method using the same.

2. Description of the Related Art

Because of their plasmonic, catalytic, electronic, and magnetic properties, metal nanostructures have been intensively studied over the past decade. Combining multiple metallic nanocomponents into a single specific nanostructure often generates unusual optical and chemical properties such as intense plasmonic coupling and higher chemical affinity, and offers wider and more diverse applications. However, synthesizing and assembling these complex nanostructures are challenging, and the use of multicomponent, multimeric metallic nanostructures is severely limited because of their synthetic inaccessibility.

Although there has been much progress in synthesizing various nanostructures, including multimetallic nanoparticles such as core-shell, tadpole-like, heterodimers at a liquid micelle interface, nanopolyhedra and nanorods (Shi, W. et al., Nano Lett., 2006, 6, 875; Wu, Y. et al., Nature, 2004, 430, 61; Lu, Y. et al., J. Am. Chem. Soc., 2003, 125, 12724; Huang, M. H. et al., Science, 2001, 292, 1897; Lassiter, J. B. et al., Nano Lett., 2008, 8, 1212), most reported methods for synthesizing heterometallic hybrid nanoparticles involve complicated procedures and harsh reaction conditions, and are unused for synthesizing a simple structure such as dimmers. Furthermore, although highly challenging, asymmetric synthesis of complex nanostructures with specific orientations could provide a new pathway for the formation of nanostructures with unprecedented properties and functions (Caswell, K. K. et al., J. Am. Chem. Soc., 2003, 125, 13914; Salem, A. K. et al., Nano Lett., 2004, 4, 1163; Gole, A. et al., Langmuir, 2005, 21, 10756; Chen, M. et al., J. Phys. Chem. B, 2006, 110, 211; Salant, A. et al., J. Am. Chem. Soc., 2006, 128, 10006; Chen, C.-L. et al., J. Am. Chem. Soc., 2010, 132, 6902).

Based on this background, the present inventors prepared nanoparticles that are composed of a gold or silver nanoparticle head part and a gold or silver nanoparticle body part, in which a plurality of oligonucleotides are bound to the surface of the head part, and a lower portion of the head part is located on a concave region in the upper portion of the body part. They found that these nanoparticles can offer platforms for DNA-based assembly of various aligned and unconventional nanostructures, and are highly applicable to the detection of DNA and an analyte associated with the onset and progression of a particular disease, thereby completing the present invention.

SUMMARY OF THE INVENTION

An object of the present invention is to provide nanoparticles in the shape of nanosnowman with a head part and a body part, which can offer platforms for DNA-based assembly of various aligned and unconventional nanostructures, and are highly applicable to the detection of DNA and an analyte associated with the onset and progression of a particular disease.

Another object of the present invention is to provide a preparation method of the nanoparticles.

Still another object of the present invention is to provide a method for detecting an analyte using the nanoparticles.

BRIEF DESCRIPTION OF THE DRAWINGS

FIG. 1A shows a schematic illustration (top) and solution color images (bottom) of Au—Ag head-body nanostructures with varying salt (NaCl) concentration;

FIG. 1B shows HR-TEM images of nanoparticles synthesized at different salt concentrations of 0.3 M (FIG. B-1), 0.1 M (FIG. B-2) and 0.003 M (b-3) and the corresponding UV-vis spectra (99FIG. B-4);

FIG. 2 shows salt-dependent reaction kinetics by varying salt (NaCl) concentration, in which the inset shows the magnified area from 0 to 30 min reaction time;

FIG. 3 shows HR-TEM images of Au—Ag head-body nanoparticles synthesized at a salt concentration of <1 nM;

FIG. 4A and 4B shows HR-TEM images of Au—Ag head-body nanoparticles synthesized without DNA at 0 M (FIG. 4A) and 0.003 M (FIG. 4B) salt concentration;

FIG. 5 shows DNA sequence-dependent reaction kinetics and TEM images of Au—Ag head-body nanoparticles synthesized with four different sequences, $A_{30}$-SH, $A_{10}$-SH, $T_{30}$-SH, and $T_{10}$-SH at 0.003 M salt concentration;

FIG. 6 shows reaction kinetics and TEM images of Au—Ag head-body nanoparticles synthesized with two different sequences, 15mer-PEG-$A_{10}$-SH and 15mer-$A_{10}$-SH at 0.003 M salt concentration;

FIG. 11 shows a high-resolution transmission electron microscopic image of Ag—Ag head-body nanoparticle with the shape of nanosnowman;

FIG. 12 shows Surface Enhanced Raman Scattering (SERS) spectra of Ag—Ag head-body nanoparticle with the shape of nanosnowman;

FIG. 17 shows a schematic illustration of the reaction mechanism for nanoparticles with a nanorod-shaped head part and a spherical Ag body part, and high-resolution transmission electron microscopic images of the formed nanostructures;

FIG. 18 shows a schematic illustration of the reaction mechanism for nanoparticles with a nanocubic head part and a spherical Ag body part, and high-resolution transmission electron microscopic images of the formed nanostructures;

FIG. 19 shows a schematic illustration of the reaction mechanism for nanoparticles with a spherical head part and a nanorod-shaped or nanocubic Ag body part, and high-resolution transmission electron microscopic images of the formed nanostructures; and FIG. 20 shows a schematic illustration of the reaction mechanism for nanoparticles with a spherical head part and a hollow Au body part, and high-resolution transmission electron microscopic images of the formed nanostructures.

DETAILED DESCRIPTION OF THE PREFERRED EMBODIMENTS

Figure 7A:
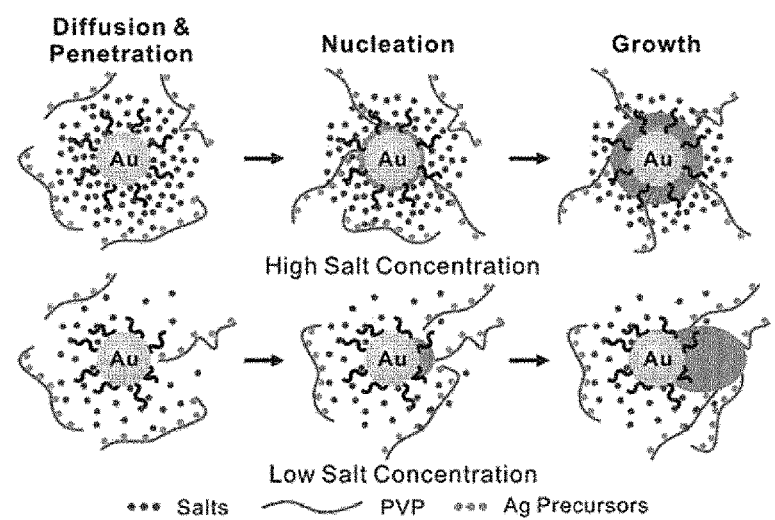
FIG. 7A and 7B shows reaction mechanism at different salt concentrations (FIG. 7A), zeta potentials for DNA-AuNPs at 0.003 M and 0.3 M salt concentrations (FIG. 7B-left), and HR-TEM images of Ag nanostructure formation on DNA-AuNPs at intermediate stages (FIG. 7B-right)

In order to achieve the above objects, the present invention provides nanoparticles that are composed of a gold or silver nanoparticle head part and a gold or silver nanoparticle body part, in which a plurality of oligonucleotides are bound to the surface of the head part, and a lower portion of the head part is located on a concave region in the upper portion of the body part.

As used herein, the term "head part" means a nanoparticle in the shape of sphere or sphere-like, nanorod or nanocube, in which oligonucleotides are bound to the surface thereof, and a lower portion thereof is in contact and connected with the body part. If the head part is in the shape of sphere or sphere-like, its diameter may be 2 nm to 200 nm. If the head part is in the shape of nanorod or nanocube, its longest axis may be 2 nm to 200 nm. The head part may be made of gold or silver.

As used herein, the term "body part" means a particle in the shape of sphere or sphere-like, nanorod or nanocube, in which the body part is in contact and connected with the lower portion of the head part. Further, the body part may be in the form of hollow particle. If the body part is in the shape of sphere or sphere-like, its diameter may be 2 nm to 900 nm. If the body part is in the shape of nanorod or nanocube, its longest axis may be 2 nm to 900 nm. The body part may be made of gold or silver.

In the present invention, the head part and the body part may be asymmetric in their sizes. Specifically, the body part may be bigger than the head part.

In the present invention, the longest axis of the nanoparticle may be 4 nm to 900 nm.

The nanoparticle of the present invention is characterized in that the head part and the body part are in contact and connected with each other to have a snowman or snowman-like structure. Therefore, a part of the oligonucleotides bound to the surface of the head part are exposed outside and the rest thereof are buried in a concave region in the upper portion of the body part. Consequently, the nanoparticle may have asymmetrically modified oligonucleotides.

As used herein, the term "oligonucleotide" refers to a polymer composed of a small number of nucleotides, and generally a short nucleotide chain that can be chemically synthesized. The oligonucleotide plays an important role in the synthesis of the nanoparticles according to the present invention. Specifically, the presence of modified oligonucleotides on the surface of the head part is critical for forming head-body structures of high yield in a controllable fashion. No particular structure with a defined shape, that is, no head-body structure can be synthesized without oligonucleotides.

The oligonucleotide may be modified with a linker compound at the 3' or 5' terminus and attached to the surface of the head part via the linker compound. As used herein, the term "linker compound" means a compound that is linked at the 3' or 5' terminus of each oligonucleotide in order to link oligonucleotides to the surface of the head part. A method of cross-linking nanoparticles via the linker compound is known in the art (Feldheim, The Electrochemical Society Interface, Fall, 2001, pp. 22-25). One end of the linker compound includes a functional group which binds to the surface of the core. Preferably, the functional group is a sulfur-containing group such as thiol or sulfhydryl (HS). The functional group may be a compound represented by RSH, an alcohol or phenol derivative in which a sulfur atom is present instead of an oxygen atom. Alternatively, the functional group may be a thiol ester or dithiol ester group which are respectively represented by RSR' or RSSR'. The functional group may be an amino group ($-NH_2$) or an alcohol group.

Further, the oligonucleotide may contain a spacer sequence between the functional group and oligonucleotide.

The spacer sequence is represented by $-PEG_x-Y_y-(CH_2)_z-$, in which x is an integer of 0 to 30, y is an integer of 0 to 30, z is an integer of 3 to 6, and Y is adenine, thymine, guanine or cytosine, respectively. Preferably, z is 3 or 6.

In this regard, if PEG is present in the spacer sequence, PEG binds to the oligonucleotide. If PEG is absent in the spacer sequence, Y binds to the oligonucleotide, and $(CH_2)_z$ at the opposite terminus binds to the functional group. In detail, the spacer sequence may be any one selected from the group consisting of $PEG_{18}-A_{10}-(CH_2)_3$, $PEG_{18}-A_{10}-(CH_2)_6$, $PEG_{18}-A_{30}-(CH_2)_3$, $PEG_{18}-A_{30}-(CH_2)_6$, $PEG_{18}-T_{10}-(CH_2)_3$, $PEG_{18}-T_{10}-(CH_2)_6$, $PEG_{18}-T_{30}-(CH_2)_3$, $PEG_{18}-T_{30}-(CH_2)_6$, $A_{10}-(CH_2)_3$, $A_{10}-(CH_2)_6$, $A_{30}-(CH_2)_3$, $A_{30}-(CH_2)_6$, $T_{10}-(CH_2)_3$, $T_{10}-(CH_2)_6$, $T_{30}-(CH_2)_3$, $T_{30}-(CH_2)_6$, $PEG-A_{10}$, $PEG-A_{10}$, $PEG-A_{30}$, $PEG-A_{30}$, $PEG-T_{10}$, $PEG-T_{10}$, $PEG-T_{30}$, and $PEG-T_{30}$, but is not limited thereto.

In the present invention, example of the oligonucleotide may include 5'-TAACAATAATCCCTC-$PEG_{18}$-$A_{10}$-$(CH_2)_3$-SH-3', (SEQ ID No: 1), 5'-HS-$(CH_2)_6$-$A_{10}$-$PEG_{18}$-ATCCTTATCAATATT-3' (SEQ ID No: 2), or 5'-CACGAGTTTCTCAAA $PEG_{18}$-$A_{10}$-$(CH_2)_3$-SH-3' (SEQ ID No: 3), but is not limited thereto.

Further, in the present invention, a Raman active molecule may bind to the oligonucleotide. As used herein, the term "Raman active molecule" refers to a molecule which facilitates the detection and measurement of an analyte by a Raman detector when the nanoparticles of the present invention are applied to one or more analytes. The Raman active molecule produces a specific Raman spectrum and has the advantage of allowing the effective analysis of subsequent biomolecules. Considering the surface enhanced scattering effect, it is preferable that the Raman active molecule binds close to the region where the oligonucleotides bind to the head part. The Raman active molecules useful in Raman spectroscopy include organic or inorganic molecules, atoms, complexes or synthetic molecules, dyes, natural dyes (phycoerythrin, etc.), organic nanostructures such as $C_{60}$, buckyballs, carbon nanotubes, quantum dots, and organic fluorescent molecules. Specific examples of the Raman active molecules may include FAM, Dabcyl, TRIT (tetramethyl rhodamine isothiol), NBD (7-nitrobenz-2-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy, fluorescein, 5-carboxy-2',4',5',7'-tetrachlorofluorescein, 5-carboxyfluorescein, 5-carboxyrhodamine, 6-carboxyrhodamine, 6-carboxytetramethyl aminophthalocyanine, azomethine, cyanine, xanthine, succinylfluorescein, aminoacridine, quantum dots, carbon nanotubes, carbon allotropes, cyanide, thiol, chlorine, bromine, methyl, phosphorus, sulfur, cyanine dyes (Cy3, Cy3.5, Cy5), and rhodamine.

Further, a variety of substances may be attached to the surface of the nanoparticles according to the present invention to improve the properties of the nanoparticles. For example, if nanoparticles are used in vivo, the surface may be modified with a biocompatible polymer. The surface of the nanoparticle according to the present invention may be functionalized with a biomolecule. When the surface of the nanoparticle according to the present invention is functionalized with a biomolecule, the nanoparticle binds to only the subject to be analyzed, so as to more improve its analytical ability. Examples of the biomolecules used for functionalizing the nanoparticle include antibodies, antibody fragments, genetically engineered antibodies, single-chain antibodies, receptor proteins, ligand proteins, enzymes, inhibitor proteins, lectins, cell-adhesion proteins, oligonucleotides, polynucleotides, nucleic acids, and aptamers.

Further, the present invention provides a method for preparing the nanoparticle, including the following steps of:
1) modifying a gold or silver nanoparticle with oligonucleotides (step 1); and
2) reacting the oligonucleotide-modified gold or silver nanoparticle with a gold or silver precursor in the presence of NaCl, a reducing agent, and a stabilizer (step 2).

Step 1) is a step of modifying the gold or silver nanoparticle with oligonucleotides, and a step of binding oligonucleotides to the surface of the gold or silver nanoparticle to form the head part.

Step 1) may be performed by a method known in the art in accordance with the known literature. In embodiments of the present invention, it was performed with reference to the literature 'Hurst, S. J. et al., Anal. Chem., 2006, 78, 8313' and 'Lim, D. -K. et al., Nature Mater., 2010, 9, 60'.

The gold or silver nanoparticles may be commercially available or prepared by the known method.

The oligonucleotides useful in step 1) are the same as those disclosed in the above description of the nanoparticle.

The gold or silver nanoparticle used in step 1) may be in the shape of sphere or sphere-like, nanorod or nanocube. The head parts may be formed in a variety of shapes by using gold or silver nanoparticle having the various shapes.

Step 2) is a step of reacting the oligonucleotide-modified gold or silver nanoparticle with the gold or silver precursor in the presence of NaCl, a reducing agent, and a stabilizer, and a step of adding the gold or silver precursor to the oligonucleotide-modified gold or silver nanoparticle constituting the head part and reacting them in the presence of NaCl, the reducing agent and the stabilizer so as to form the body part.

In the present invention, the gold precursor may be any compound containing Au ion, such as $HAuCl_4$. Further, the silver precursor may be any compound containing Ag ion, and preferably $AgNO_3$ or $AgClO_4$.

An Au—Ag head-body nanoparticle, an Au—Au head-body nanoparticle, or an Ag—Ag head-body nanoparticle may be prepared by the above preparation method. In particular, the present invention is characterized in that more clearly defined head-body nanosnowman structures can be obtained by lowering the NaCl concentration. The NaCl concentration may be preferably 1 nM to 0.1 M, more preferably 0.001 M to 0.05 M, and most preferably 0.003 M. In addition, the Au—Au head-body nanoparticle may be prepared in the more defined head-body nanosnowman structure by controlling pH of step 2). Specifically, step 2) may be performed at pH 2 to 8, and preferably at pH 2 to 7.

In the present invention, the reducing agent may be hydroquinone, sodium borohydride ($NaBH_4$), sodium ascorbate, hydroxyl amine or a combination thereof, but is not limited thereto.

In the present invention, the stabilizer may be a material containing nitrogen or oxygen having a lone pair of electrons, or both of them. It may be exemplified by derivatives including pyrrolidine, imidazolidine, pyrazolidine, piperidine, piperazine, sorbitol, ethylene glycol or a carbonyl group; saccharoses including glucose or fructose; DNA; PNA; or RNA, and preferably polyvinylpyrrolidone (PVP).

Further, the body part may be prepared in various shapes of sphere or sphere-like, nanorod or nanocube by changing a molar ratio between the reducing agent and the gold or silver precursor, and a molar ratio between the number of PVP repeating units as the stabilizer and the gold or silver precursor. Furthermore, the body part may be more easily prepared in the shape of nanocube by changing the addition rate of the gold or silver precursor.

In step 2) of the present invention, pure water or phosphate buffer may be used as a solvent.

In the present invention, the reaction temperature of step 2) may be 10 to 100° C. If the reaction temperature is lower than 10° C., too much time is required for the preparation of the body part. If the reaction temperature is higher than 100° C., less uniform body parts are formed.

In the present invention, the reaction time of step 2) may be properly controlled within 10 to 24 hours according to the reaction temperature.

In the present invention, hollow body parts may be formed by galvanic replacement after step 2).

In one embodiment of the present invention, Au—Ag head-body structures were synthesized, and then 0.01 M cetyltrimethylammonium chloride (CTAC) and 0.05 mM Gold (III) chloride trihydrate ($HAuCl_4 \cdot 3H_2O$) in deionized water were used to form Au—Au head-body (hollow) structures by galvanic replacement. As galvanic replacement was carried out, silver in the body part is replaced with gold to have hollow structures.

In the present invention, nanoparticles may be prepared in various shapes by altering the concentration of gold or silver precursor, the molar ratio between the reducing agent and the gold or silver precursor, the molar ratio between the number of PVP repeating units as the stabilizer and the gold or silver precursor, or the addition rate of the gold or silver precursor. Further, imaging effects can be increased by preparing nanoparticles with complex structures of various shapes.

Further, the present invention provides a method for detecting an analyte, including the steps of functionalizing the surface of the nanoparticle according to the present invention with a biomolecule capable of recognizing the analyte; exposing the nanoparticles to a sample containing one or more analytes; and detecting and identifying one or more analytes by laser excitation and Raman spectroscopy.

Examples of the analyte may include amino acids, peptides, polypeptides, proteins, glycoproteins, lipoproteins, nucleosides, nucleotides, oligonucleotides, nucleic acids, saccharides, carbohydrates, oligosaccharides, polysaccharides, fatty acids, lipids, hormones, metabolites, cytokines, chemokines, receptors, neurotransmitters, antigens, allergens, antibodies, substrates, metabolites, co-factors, inhibitors, drugs, pharmaceutical substances, nutrients, prions, toxins, toxic substances, explosive substances, pesticides, chemical weapon agents, biologically noxious agents, radioactive isotopes, vitamins, heterocyclic aromatic compounds, oncogenic agents, mutagenic factors, anesthetics, amphetamine, barbiturate, hallucinogens, wastes, and contaminants. If the analytes are nucleic acids, they may include genes, viral RNAs and DNAs, bacterial DNAs, fungal DNAs, mammal DNAs, cDNAs, mRNAs, RNA and DNA fragments, oligonucleotides, synthetic oligonucleotides, modified oligonucleotides, single- and double-stranded nucleic acids, and natural or synthetic nucleic acids.

Examples of the biomolecules functionalizing the nanoparticle may include antibodies, antibody fragments, genetically engineered antibodies, single-chain antibodies, receptor proteins, ligand proteins, enzymes, inhibitor proteins, lectins, cell-adhesion proteins, oligonucleotides, polynucleotides, nucleic acids, and aptamers. The functionalization may be carried out by attaching the biomolecules on the surface of nanoparticles through an electrostatic attractive force, or directly binding them to each other, or using a linker. The functionalization method is not particularly limited.

Preferably, the analyte of the present invention may be detected or identified by any known Raman spectroscopy, preferably, Surface Enhanced Raman Scattering (SERS), Surface enhanced resonance Raman spectroscopy (SERRS), hyper-Raman and/or Coherent Anti-Stokes Raman Spectroscopy (CARS).

As used herein, the term "Surface Enhanced Raman Scattering" (SERS) refers to a spectroscopic method utilizing a phenomenon in which when molecules are adsorbed on a roughened surface of a particular metal or are present within a distance of hundreds of nanometers from a surface, in which the intensity of Raman scattering is dramatically increased to the level of $10^6$-$10^8$ times compared with normal Raman signals. The term "Surface Enhanced Resonance Raman Spectroscopy" (SERRS) refers to a spectroscopic method utilizing a phenomenon in which the adsorbate at a SERS active surface is in resonance with the laser excitation wavelength. The term "Coherent Anti-Stokes Raman Spectroscopy" (CARS) refers to a spectroscopic method in which two laser beams, variable and fixed, are incident on a Raman active medium to generate a coherent anti-Stokes frequency beam.

In an embodiment used in practice, the Raman active substrate may be operably linked with one or more Raman detection unit devices. Raman spectroscopy-based methods detecting analytes are well known in the art (e.g., U.S. Pat. Nos. 6,002,471, 6,040,191, 6,149,868, 6,174,677, and 6,313,914). In SERS and SERRS, the intensity of Raman scattering from molecules absorbed on a roughened metal surface such as silver, gold, platinum, copper or aluminum is increased by $10^6$ fold or higher.

Non-limiting examples of the Raman detection apparatus are disclosed in U.S. Pat. No. 6,002,471. The excitation light is generated by either a Nd:YAG laser at 532 nm wavelength or a Ti:sapphire laser at 365 nm wavelength. Pulsed laser beams as well as continuous beams can be used. The light excitation signal passes through confocal optics and the microscope objective, and is focused onto a Raman active substrate containing one or more analytes. The Raman light emitted from the analyte is collected by the microscope objective and the confocal optics, and is coupled to a monochromator for spectral dissociation. The confocal optics includes a combination of dichroic filters, barrier filters, confocal pinholes, objective lenses, and mirrors, and serves the purpose of reducing the background signal. Standard full field optics as well as confocal optics can be used. The Raman emission signals are detected by a detector system which includes an avalanche photodiode interfaced with a computer for counting and the digitization of the signals.

Another example of the detection apparatus may be found in U.S. Pat. No. 5,306,403 in which the SERS measurements can be conducted with a Spex Model 1403 double-grating spectrometer equipped with a gallium-arsenide photomultiplier tube (RCA Model C31034 or Burle Industries Model C3103402) which is operated in single-photon counting mode. The excitation source is a 514.5 nm line argon-ion laser (SpectraPhysics, Model 166) and a 647.1 nm line of a krypton-ion laser (Innova 70, Coherent).

Other lasers available for excitation include the nitrogen laser (Laser Science Inc.) at 337 nm, and the helium-cadmium laser (Liconox) at 325 nm (U.S. Pat. No. 6,174,677), photodiodes, Nd:YLF laser, and/or various ion lasers and/or dye lasers. The beams are spectrally purified with a bandpass filter (Corion) and collimated before being focused onto a Raman active substrate with a 6× objective lens (Newport, Model L6×). Furthermore, the objective lens is used both to excite the analyte and to collect the Raman signals in order to create a right angle shape of the excited beam and released Raman signals. This end-on excitation/collection geometry was made possible by using a holographic beam splitter (Kaiser Optical Systems, Inc., Model HB 647-26N18). A holographic notch filter (Kaiser Optical Systems, Inc.) can be placed to further reject Rayleigh scattered radiation. Another Raman detector is a spectrograph (ISA, HR-320) equipped with a red-enhanced intensified charge-coupled device (RE-ICCD) detection system (Princeton Instruments). Other detectors such as a Fourier transform spectrometer (based on Michelson interferometer), a charged injection device, photodiode arrays, InCaAs detectors, electron-multiplying CCD, highly sensitive CCD and/or phototransistor arrays may be used.

Any well-known suitable form or modification of Raman spectroscopy or related spectrometry may be used for the detection of analytes. Examples thereof include normal Raman scattering, resonance Raman scattering, surface enhanced Raman scattering, surface enhanced resonance Raman scattering, coherent anti-Stokes Raman spectroscopy (CARS), stimulated Raman spectroscopy, inverse Raman spectroscopy, stimulated gain Raman spectroscopy, hyper-Raman scattering, molecular optical laser examiner (MOLE), Raman microprobing, Raman microscopy, confocal Raman microspectrometer, 3-D or scanning Raman, Raman saturation spectroscopy, time resolution resonance Raman, Raman dissociation spectroscopy, and UV-Raman microscopy, but are not limited thereto.

In a specific embodiment of the present invention, the Raman detection apparatus may be operably linked to a computer. Data from the detection apparatus may be processed by the processor and stored in the main memory device. Data on the emission profiles for standard analytes may be stored on the main memory device or ROM. The processor can identify the analyte from the sample by comparing emission spectra from the analyte in the Raman active substrate. The processor can analyze the data from the detection apparatus to identify and/or measure concentration level of various analytes. Differently set computers may be used to serve different purposes. Hence, the structure of the system may differ from one embodiment to another. After being collected, data are typically transferred to a device where data are analyzed. For data analysis, the data from the detector are processed by a digital computer as described above. Typically, the computer is programmed to receive and store the data from the detector as well as analyze and report the data.

Further, the present invention provides a kit for detecting an analyte, including the nanoparticles according to the present invention. The detection kit includes general tools and reagents well known in the art. Examples of the tools/reagents include a carrier, a labeling substance capable of producing a detectable signal, a dissolving agent, a washing agent, a buffered solution, and a stabilizer, but are not limited thereto. If the labeling substance is an enzyme, a substrate for measuring the activity of the enzyme and a reaction terminator may be included. Examples of the carrier include, but are not limited to, soluble carriers, for example, a well-known, physiologically acceptable buffer, e.g., PBS, insoluble carriers, for example, polystyrene, polyethylene, polypropylene, polyester, polyacrylonitrile, fluorine resin, crosslinked dextran, polysaccharides, polymers such as magnetic beads in which latex is coated with metal, paper, glass, agarose or a combination thereof.

The nanoparticles according to the present invention can be an alternative to nanoparticles that are used in the conventional chip-based molecular diagnostics or imaging diagnosis. Therefore, it is possible to apply the nanoparticles according to the present invention to chip-based molecular diagnostics such as DNA chips, protein chips or the like. Examples of the analytes to be detected are genes, viral RNAs and DNAs, bacterial DNAs, fungal DNAs, mammal DNAs, cDNAs, mRNAs, RNA and DNA fragments, oligonucleotides, synthetic oligonucleotides, modified oligonucleotides, single- and double-stranded nucleic acids, and natural and synthetic nucleic acids, amino acids, peptides, polypeptides, proteins, glycoproteins, lipoproteins, nucleosides, nucleotides, oligonucleotides, nucleic acids, saccharides, carbohydrates, oligosaccharides, polysaccharides, fatty acids, lipids, hormones, metabolites, cytokines, chemokines, receptors, neurotransmitters, antigens, allergens, antibodies, substrates, metabolites, co-factors, inhibitors, drugs, pharmaceutical substances, nutrients, prions, toxins, toxic substances, explosive substances, pesticides, chemical weapon agents, biologically noxious agents, radioactive isotopes, vitamins, heterocyclic aromatic compounds, oncogenic agents, mutagenic factors, anesthetics, amphetamine, barbiturate, hallucinogens, wastes, and contaminants.

Further, the nanoparticles of the present invention finds application in molecular diagnostics or imaging diagnosis, including the detection of analytes such as DNA and proteins (biomarkers) associated with the onset and progression of a particular disease, large-scale genome sequence analysis, single-nucleotide polymorphism (SNP) detection, base sequencing, gene fingerprinting, disease relationship, and drug development.

Further, the nanoparticles according to the present invention include a substance capable of emitting different signals inside or outside the surface thereof. For example, they may further include a CT contrast agent, an MRI contrast agent, an optical imaging contrast agent, an ultrasound contrast agent or a combination thereof. Therefore, CT, MRI, optical imaging, or ultrasound analysis, as well as Raman spectroscopy by the nanoparticles can be performed at the same time.

Further, the nanoparticles according to the present invention may include genes, antibodies, drugs or the like, and thus the nanoparticles are used as a drug carrier for the treatment of diseases.

Hereinafter, the constitution of the present invention will be described in detail with reference to the drawings.

The present invention provides a DNA-based approach for the synthesis of Au—Ag head-body "nanosnowman" particles in a high yield (>95%) by simple control of the salt concentration (NaCl concentration in one embodiment) under aqueous conditions (FIG. 1).

The asymmetric growth of a silver nanoparticle (AgNP) on the surface of a DNA-modified gold nanoparticle (DNA-AuNP) was observed, as a lower salt concentration was applied to the reaction solution. Importantly, it was shown that these nanosnowman particles with asymmetrically modified DNA can be used as building blocks for the oriented assembly of various complex nanostructures. Typically, when Ag-shell-forming agents are added to DNA-AuNPs, spherical Au—Ag core-shell structures are formed (Lim, D. -K. et al., Chem. Comm., 2008, 5312; Lim, D. -K. et al., Nature Mater., 2010, 9, 60; Lim, D. -K. et al., Nature Nanotech., 2011, 6, 452). However, it have been found that anisotropic Au—Ag head-tail nanosnowman structures can be obtained simply by lowering the salt concentration and adding a proper reducing agent and polymer for the process of AgNP budding on the DNA-AuNP surface. DNA on the AuNP surface offers high particle stability, efficient surface protection, and controllability of oriented particle growth. The reaction rate for Ag growth on the Au surface is much higher at lower salt concentrations and that salts can reduce the repulsive force between the DNA strands on AuNPs (Hurst, S. J. et al., Anal. Chem., 2006, 78, 8313), suggesting that lower salt concentrations free the space between DNA strands on the AuNP surface and allow Ag precursors to be controlled on the nucleation sites more readily. Once Ag structures are budded on any site of the Au surface, it is much easier for Ag to be deposited at the already-formed Ag site. Interestingly, as a result of this asymmetric growth, DNA strands were buried on the side with Ag growth, while the other Au surface without Ag budding had exposed DNA that could hybridize. These nanosnowman particles with asymmetrically modified DNA can offer platforms for DNA-based assembly of various aligned and unconventional nanostructures. Therefore, the present invention provides a new understanding and pathway for the synthesis of anisotropic nanostructures and assembly and application of nanostructured materials.

Hereinafter, the present invention will be described in detail with reference to the following Examples. However, the following Examples are for illustrative purposes only, and the invention is not intended to be limited by these Examples.

EXAMPLE 1

Materials and Methods

Materials

All the chemical reagents [AgNO$_3$, polyvinylpyrrolidone (MW 40,000 and 10,000 K value: 29-32), (+)-sodium L-ascorbate, hydroxyl amine, dithiothreitol and sodium dodecyl sulfate] were purchased from the Sigma-Aldrich (St. Louis, Mo., USA) and used without further purification. Au nanoparticles (AuNPs) were purchased from Ted Pella, Inc. (Redding, Calif., USA). HPLC-purified oligonucleotides and NAP-5 column were purchased from IDT, Inc. (Coralville, Iowa, USA) and GE Healthcare (Sephadex G-25 medium, DNA grade), respectively. NANOpure water (>18.0 MΩ, Milli-Q) was used for all the experiments.

Methods

HR-TEM Analysis

The formvar/carbon-coated copper grid (Ted Pella, Inc. Redding, Calif., USA) and HR-TEM (JEOL, Japan, 300 kV) were used for the HR-TEM analysis.

Preparation of DNA-modified Gold Nanoparticles

Oligonucleotides on gold nanoparticles (AuNPs) were modified and characterized based on literature procedures (Hurst, S. J. et al., Anal. Chem., 2006, 78, 8313; Lim, D. -K. et al., Nature Mater., 2010, 9, 60). Oligonucleotides were reduced by dithiothreitol (DTT, 0.1 M) in phosphate buffer (0.17 M, pH=8.0) and then purified using a desalting NAP-5 column. For the preparation of DNA modified gold nanoparticles, purified DNA [5'-TAACAATAATCCCTC-PEG$_{18}$-A$_{10}$-(CH$_2$)$_3$-SH-3'] (SEQ ID NO: 1) were mixed with 30-nm AuNP solution. The loading number of DNA, which is ~200 strands per 30 nm gold nanoparticle, was decided based on the literature (Lim, D. -K. et al., Nature Mater., 2010, 9, 60). In details, 193 μl of 44.9 μM DNA solution was mixed in 5 mL of 1.0 nM AuNP solution. The excess amount of DNA (30-fold more) was added for DNA-modification process. The mixtures were adjusted to obtain a final phosphate concentration of 10 mM (pH 7.4) with 100 mM phosphate buffer. The resulting solution was wrapped in a foil and placed on an orbital shaker at room temperature for 60 min. Next, the mixtures were adjusted to 0.3 M NaCl (0.05 M×2 and 0.1 M×2) by the addition of salting buffer (2 M NaCl, 10 mM PB) every 20 min and heated for 5 min in a water bath at 70° C. after each step to minimize the interactions of DNA bases and gold surface. After the salt-aging process, the solution was incubated overnight at room temperature. The solution was then centrifuged at 10,000 rpm for 15 min and the supernatant was removed carefully to remove unmodified DNA and to lower salt concentration. The precipitate was redispersed in 10 mM PB solution (pH 7.4; this procedure was repeated five times). For example, when 1 mL of DNA-modified solution was centrifuged at 10,000 rpm for 15 min, 20 μL of solution containing precipitates were remained after the supernatant was removed and redispersed in 10 mM PB of 980 μL. As a result, the final concentration of salt was adjusted to ~1 nM after repeated washing process (5 times). Finally, the precipitate was redispersed in a desired PBS solution from 0.3 M to 0.1 M, 0.003 M NaCl (10 mM PB, pH 7.4). These DNA modified gold nanoparticles were used as seeds for asymmetric Ag nanostructure growth. The concentration of DNA-modified gold nanoparticles was characterized using the UV-Vis spectrophotometer (Agilent 8453 spectrophotometer, USA).

For the preparation of single complementary DNA$_2$-modified 13-nm gold nanoparticles, premixed probe DNA$_2$ [5'-HS-(CH$_2$)$_6$-A$_{10}$-PEG$_{18}$-ATCCTTATCAATATT-3'] (SEQ ID NO: 2) and protecting DNA [5'-CACGAGTTTCT-CAAA-PEG$_{18}$-A$_{10}$-(CH$_2$)$_3$-SH-3'] (SEQ ID NO: 3) were conjugated to gold nanoparticles. The loading number of DNA was controlled stoichiometrically ([protecting DNA]: [probe DNA]=69:1 for 13-nm gold nanoparticles based on literature procedures) (Hurst, S. J. et al., Anal. Chem., 2006, 78, 8313; Lim, D. -K. et al., Nature Mater., 2010, 9, 60). The excess amount of DNA (~30-fold more than the number of gold nanoparticles) was added for DNA-modification process. For example, 656.1 μL (31.0 μM) of protecting DNA and 51.1 μL (5.8 μM) of probe DNA$_2$ were added in 2 mL (4.9 nM) of 13 nm gold nanoparticles. The mixtures were adjusted to 0.3 M NaCl by the same procedure as described above.

EXAMPLE 2

Preparation of Au—Ag Head-body Nanoparticles with the Shape of Nanosnowman

The nanosnowman structures were synthesized by using DNA-AuNPs prepared in Example 1 as seeds and adding Ag precursors and other reagents to grow Ag structures on the DNA-AuNP surface.

Au—Ag head-body nanosnowman structures were synthesized using 1% polyvinylpyrrolidone (PVP), 0.1 M (+)-sodium L ascorbate (L-SA) and 1 mM silver nitrate (AgNO$_3$) in deionized water by a polymer-aided chemical reduction method. The PVP, L-SA, and Ag precursors were added sequentially to the DNA-modified AuNP seed solution prepared in Example 1. The molar ratio between the reducing agent and Ag$^+$ (L-SA/Ag) was kept at 50 and the molar ratio between the number of PVP repeating units and Ag$^+$ (PVP/Ag) was kept at 30. Typically, 100 μL of 0.2 nM DNA AuNPs was reacted with 59.4 μL of 1 mM AgNO$_3$ solution in the presence of 19.8 μL of 1% PVP and 29.7 μL of 0.1 M L-SA at room temperature, respectively. The resulting mixture was mildly shaken in an orbital shaker. After reaction is finished, the solution was centrifuged at 8,000 rpm for 7 min to eliminate any un-reacted residues and then redispersed in deionized water.

EXAMPLE 3

Structural Changes of Nanoparticles Depending on Salt Concentration

When the salt concentration was varied from high to very low values (0.3 M, 0.1 M, and 0.003 M NaCl), different solution colors ranging from yellow to orange, dark-green, and bright green were observed (FIG. 1A), along with a structural transformation from spherical Au—Ag core-shell particles to Au—Ag head-body nanosnowman particles.

The formed nanostructures were confirmed by high-resolution transmission electron microscopy (HR-TEM; JEOL, Japan, 300 kV) and UV-vis spectroscopy (Agilent 8453 spectrophotometer, USA). FIG. 1B shows the HRTEM images of nanostructures obtained from reactions with different salt concentrations. FIG. 1B shows the structural changes from spherical particles to snowman-like nanostructures. The UV-vis data (FIG. 1B-4) show that the plasmonic peaks of the nanostructures were strongly affected by varying the salt concentration, with a new plasmonic band appearing at 630 nm at a very low salt concentration. In general, the intensity of the resonance peak increases when charges separate with mirror symmetry because this provides the main restoring force for electron oscillation. Therefore, in general, the intensity of the longitudinal peak is higher than that of the transverse peak because of the increase in the effective dipole moment of the particle, which is larger if charges separate with mirror symmetry. One possible reason why the amplitude of the longitudinal band is lower than that of transverse mode in the present invention is that mirror symmetry of a nanosnowman structure is not fully isotropic, and the Au—Ag bimetal composition could also affect the anisotropy of the mirror symmetry (Tan, S. J. et al., Nature Nanotech, 2011, 6, 268; Wiley, B. J. et al., J. Phys. Chem., 2006, 110, 15666).

Asymmetric Ag growth on the surfaces of the AuNPs can be clearly seen in the images in FIGS. 1B-2 and 1B-3, but snowman nanostructures were more reproducibly grown in a much higher yield for the very low salt case (FIG. 1B-3). The lengths of the longest axes for the spherical core-shell, intermediate nanosnowmen, and nanosnowmen were approximately 46, 50, and 64 nm, respectively (200 particles were measured for each case).

The TEM results for the structural changes were well-matched with the UV-vis results, which showed that the appearance of the surface plasmon resonance (SPR) bands changed from spherical shape to rod or dimeric shapes as the salt concentration decreased (FIG. 1B-4). Secondary SPR modes, which are associated with the longitudinal axis, are known to shift to longer wavelengths as the nanoparticle shape gets longer (e.g., rod and dimeric shapes) (Lassiter, J. B. et al., Nano Lett., 2008, 8, 1212).

EXAMPLE 4

Salt-dependent Reaction Kinetics

The salt-dependent reaction kinetics was studied by UV-vis spectroscopy to investigate the reaction mechanism and the roles of DNA and salt concentration.

While the salt concentration was altered, the same amounts of PVP, L-SA, and Ag precursors as well as the same temperature (room temperature) were used and maintained for all of the experiments.

FIG. 2 shows changes in the absorbance at 400 nm as a function of time for three cases with different salt concentrations (0.3 M, 0.1 M and 0.003 M NaCl). The UV-vis spectra were measured at 1 min intervals. Overall, the results show that the reaction rate drastically increased as the salt concentration decreased from 0.3 to 0.003 M. The times required for reaction completion were approximately 15 min, 3 h, and 5 h for 0.003 M, 0.1 M and 0.3 M NaCl, respectively. Reaction was completed very fast, especially at very low salt concentration (see FIG. 2 inset). This fast kinetics for 0.003 M NaCl in forming nanosnowman particles suggests that fast nucleation and growth of Ag on the AuNP surface is critical in forming a specific nanostructure in a high yield and that a low salt concentration facilitates this process. In the case of nearly no salt condition (<1 nM), the reaction was finished within ~2 min. TEM image analysis showed that nanosnowman structures were formed only partially and that many other structures, including spherical core-shell particles and irregularly shaped nanostructures, were also formed as a result of the uncontrollably fast reaction kinetics (FIG. 3). These results suggest that low concentration is preferred for faster kinetics and formation of uniform nanosnowman structures in a high yield but also that the reaction becomes uncontrollable and generates rather random nanostructures when there is nearly no available salt in solution.

EXAMPLE 5

Effects of DNA and Presence of Salt on Nanoparticle Formation

Reactions were performed using AuNPs without DNA modification at two different salt concentrations (0.003 M and no salt) to see the effect of DNA and its correlation with the presence of salt. Without salt, the reaction was finished within a few seconds, and Ag structures were grown and budded from AuNP surface in many different directions with irregular shapes (FIG. 4A). With 0.003 M salt, although the reaction rate was slowed (~15 min) and more directional growth of Ag from AuNP surface was observed, no particular structure with a defined shape was synthesized without DNA (FIG. 4B). These results show that the presence of DNA on the AuNP surface is critical in forming nanosnowman structures in a high yield in a controllable fashion and again that salt adjustment is an important handle to drive the directional growth of Ag structures on AuNP surfaces.

EXAMPLE 6

Influence of PEG or DNA Sequences on Nanoparticle Formation

To confirm the influence of PEG or DNA sequences on Ag growth, five different DNA sequences ($A_{30}$-SH, $A_{10}$-SH, $T_{30}$-SH, and $T_{10}$-SH for the DNA sequence effect and 15-mer-PEGA$_{10}$-SH and 15-mer-A$_{10}$-SH for the PEG effect) were used for experiments.

The results are shown in FIGS. 5 and 6.

It was reported that A binds more strongly to the Au surface than T and that poly-A DNA results in a smaller amount of loading per AuNP than poly-T DNA (Storhoff, J. J. et al., Langmuir, 2002, 18, 6666). FIG. 5 shows that the resulting nanosnowman structures were similar, but poly-A generated faster kinetics than poly-T. This becomes clearer because the longer $A_{30}$ or $T_{30}$ sequence induced faster kinetics than the $A_{10}$ or $T_{10}$ sequence. In the case of PEG, the number of modified DNA per AuNP was increased by inserting PEG into the thiolated DNA sequence (Hurst, S. J. et al., Anal. Chem., 2006, 78, 8313). These results show that addition of PEG slows the Ag budding kinetics (FIG. 6).

EXAMPLE 7

Influence of PVP on Nanoparticle Formation

To examine the role of PVP on Ag growth, nanoparticle formation depending on the presence of PVP was analyzed.

As a result, Ag deposition on the AuNP surface did not occur without PVP. It is well-known that PVP can harness and carry Ag ions via chelation by donation of lone-pair electrons of oxygen or nitrogen atoms of PVP, forming coordination complexes in aqueous solution (Zhang, Z. et al. J. Solid State Chem., 1996, 121, 105). Furthermore, Ag ions can form precipitates of AgCl without PVP because there are many chloride ions, but no precipitates were observed in solution.

EXAMPLE 8

Reaction Mechanism for Formation of Au—Ag Head-body Nanoparticle with Nanosnowman Shape On the basis of the results of Examples 3 to 7, it was proposed that the reaction mechanism for asymmetric growth of Ag nanostructures on AuNP surfaces to form Au—Ag nanosnowmen is the same as in FIG. 7A.

It is well-known that salts can reduce the repulsive forces between DNA strands, increase the DNA loading on the AuNP surface, and induce more straightened and uniform DNA structures (Hurst, S. J. et al., Anal. Chem., 2006, 78, 8313). At a lower salt concentration, a smaller amount of salt exists around the AuNPs and less uniform DNA structures are formed on the AuNP surface. The salt distribution and DNA structures on AuNPs are critical factors in Ag structure growth on DNA-AuNPs, especially when Ag precursors are carried by bulky PVP to the AuNP surface for nucleation and subsequent Ag structure growth.

As shown in FIG. 7A (top scheme), at a high salt concentration, salt can be densely packed around the DNA-AuNPs to form a passivation layer, and the DNA strands are rather uniformly distributed around the AuNPs. Thus, at high salt concentration, it is difficult for Ag-PVP complexes to penetrate through this salt layer, and slower reaction kinetics is observed. As a result of the uniformity of the DNA structures, multiple nucleation sites formed slowly and simultaneously, affording Au—Ag core-shell nanospheres. In contrast, at a low salt concentration, less uniform DNA structures can be formed on the AuNP surface, facilitating the introduction of Ag-PVP in a certain direction, and a less dense, imperfect salt layer is formed around the DNA-AuNPs (FIG. 7 a, bottom scheme). Ag-PVP complexes can more readily approach the AuNP surface, and once an Ag nucleation site forms, Ag in approaching Ag-PVP complexes should be preferentially deposited at the already-formed Ag site, resulting in faster reaction kinetics and directional growth of the Ag nanostructure on the AuNP surface.

Figure 7B:
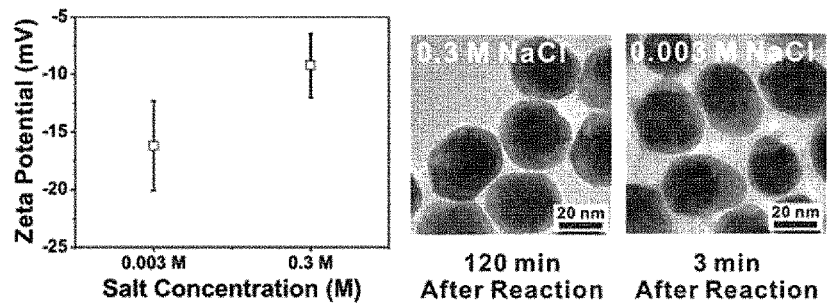

The zeta potential was more negative at lower salt concentration, and taking into account that DNA phosphate backbones are negatively charged and salt between the DNA strands creates a charge-screening effect, the results suggest that a smaller amount of salt is distributed around the DNA-AuNPs at lower salt concentration (FIG. 7B).

Furthermore, there is less $Cl^-$ ion at the low salt concentration, which could affect the chemical equilibrium ($Ag^+$+ $Cl^- \leftrightarrows AgCl$). The proposed mechanism is further supported by the HR-TEM images of particles during intermediate stages (120 and 3 min after reaction initiation using 0.3M and 0.003 M NaCl, respectively) (FIG. 7B). The TEM images show that the Ag shell grew rather uniformly all around the Au surface for 0.3 M NaCl, while an asymmetric Ag budding process was observed for the case of 0.003 M NaCl. During the growth step, the reduction of Ag precursors occurs preferentially at the nucleation sites, as it is much easier for Ag to be deposited on a pre-existing nucleation site after the initial nucleation step (Gu, H. et al., J. Am. Chem. Soc., 2005, 127, 34; Gu, H. et al., J. Am. Chem. Soc., 2004, 126, 5664).

EXAMPLE 9

Preparation of Oriented Assemblies using Nanoparticles of the Present Invention

Figure 8A:
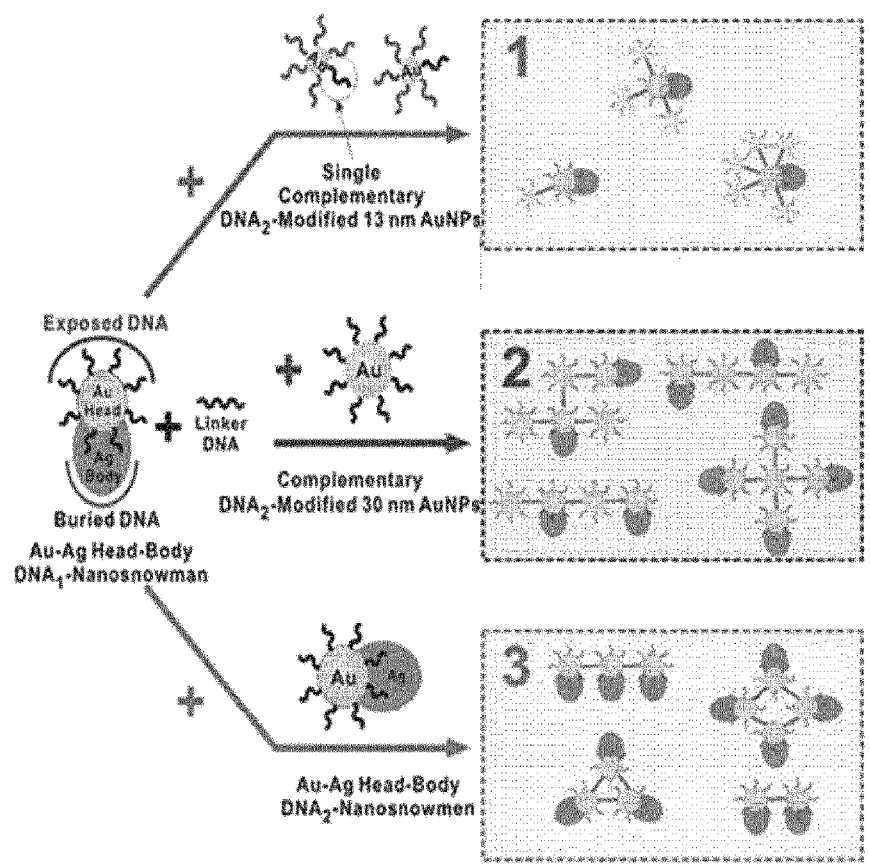
FIG. 8A shows a schematic illustration of the processes for directional assembly of DNA-nanosnowmen with asymmetric DNA modification.

It can be readily noticed that DNA-nanosnowman particles have not only asymmetrically grown nanostructures but also asymmetric DNA modification on their surfaces. On the Au head side, DNA is exposed and can be readily hybridized to complementary DNA. On the other hand, on the Ag body side, the DNA is buried within the Ag structure, and complementary DNA coupling is not possible (FIG. 8A). Using this asymmetric feature, directional assemblies of various unique nanostructures can be provided.

Figure 8B:
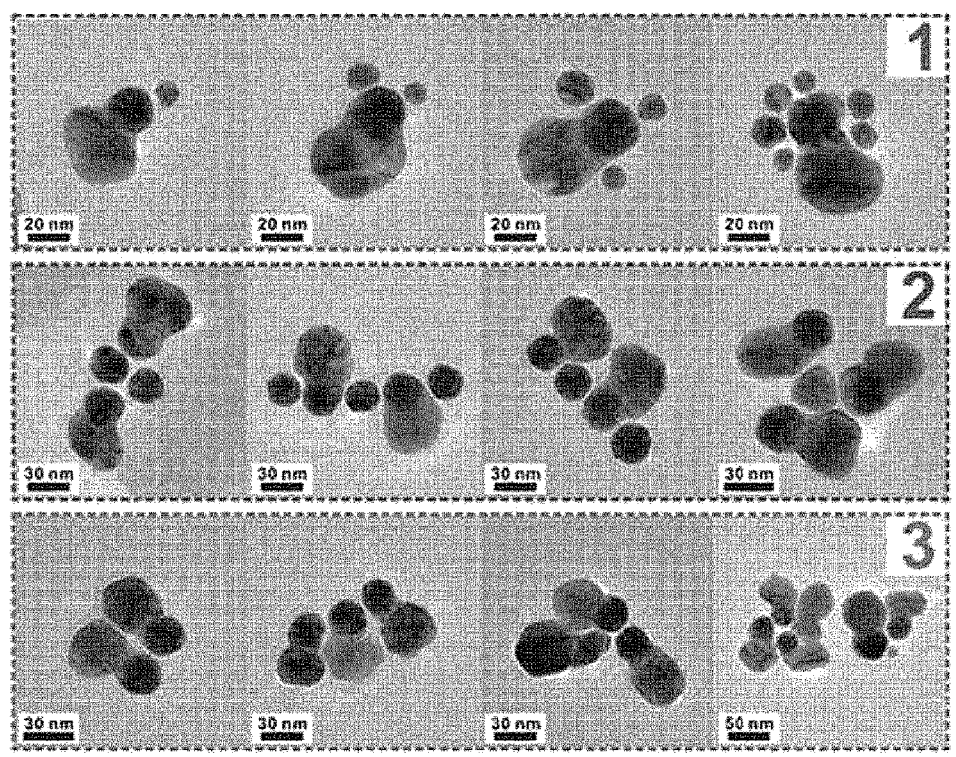
FIG. 8B shows HR-TEM images of the assembled nanostructures.

First, single complementary $DNA_2$-modified AuNPs (13 nm in diameter, Au-5'-HS-$(CH_2)_6$-$A_{10}$-$PEG_{18}$-ATCCTTAT-CAATATT-3') (SEQ ID NO: 2) were added to $DNA_1$-nanosnowman (5'-TAACAATAATOCCTC-$PEG_{18}$-$A_{10}$-$(CH_2)_3$-SH-3'-Au) (SEQ ID NO: 1). An excess amount of linker DNA (5'-GAGGGATTATTGTTAAATATTGATAAG-GAT-3' (SEQ ID NO: 4), 10000-fold higher amount than AuNP concentration), which links two half-complementary DNA-modified nanoparticles, was used to hybridize the DNA-modified nanoparticles in 0.15 M PBS solution. FIG. 8B-1 shows HR-TEM images of structures assembled with $DNA_1$-nanosnowmen and single complementary $DNA_2$-modified AuNPs. These results show that the 13 nm AuNPs are specifically assembled to the Au head regions. When complementary $DNA_2$-modified AuNPs (30 nm in diameter) were added to $DNA_1$-nanosnowmen, oriented assemblies of various nanostructures were observed via preferential binding of AuNPs to Au head parts in nanosnowmen (FIG. 8B-2). Finally, $DNA_2$-nanosnowmen and linker DNA were added to $DNA_1$-nanosnowmen. Again, highly oriented nanoassembly structures were formed via preferential binding between Au head parts of DNA nanosnowman particles (FIG. 8B-3).

EXAMPLE 10

Preparation of Au—Au Head-body Nanoparticles with the Shape of Nanosnowman

The nanosnowman structures were synthesized by using DNA-AuNPs (20 nm gold nanoparticles) prepared in Example 1 as seeds and adding Au precursors and other reagents to grow Au structures on the DNA-AuNP surface.

Au—Au head-body nanosnowman structures were synthesized using 1% polyvinylpyrrolidone (PVP), 0.1 M (+)-sodium L ascorbate (L-SA) or hydroxyl amine (HA) and 1 mM $HAuCl_4$ in deionized water by a polymer-aided chemical reduction method. The PVP, HA, and Au precursors were added sequentially to the DNA-modified AuNP seed solution prepared in Example 1. The molar ratio between the reducing agent and $Au^+$ (HA/Au) was kept at 50 and the molar ratio between the number of PVP repeating units and $Au^+$ (PVP/Au) was kept at 2. Typically, 100 μL of 0.2 nM DNA AuNPs was reacted with 10.4 μL of 1 mM $HAuCl_4$ solution in the presence of 3.5 μL of 1% PVP and 4.2 μL of 0.005 M HA at room temperature, respectively. The resulting mixture was mildly shaken in an orbital shaker. After reaction is finished, the solution was centrifuged at 8,000 rpm for 7 min to eliminate any un-reacted residues and then redispersed in deionized water.

EXAMPLE 11

Size Changes of Nanoparticles Depending on Addition Amount of Precursor

Au—Au head-body nanoparticles with the shape of nanosnowman were prepared in the same manner as in Example 9, except that the addition amounts of the gold precursor, namely, 1 mM $HAuCl_4$ solution were 5.3 μl (A-2), 10.4 μl (A-3) and 36.3 μl (A-4), instead of 1.5 μl (A-1).

Figure 9A:
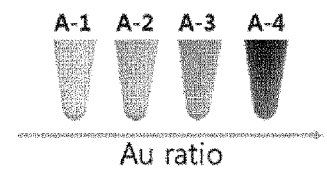
FIG. 9A shows changes in the solution color by increasing additional amount of precursors.

As the addition amount of the gold precursor increased (from A-1 to A-4), the color of the solution became dark (FIG. 9A).

The formed nanostructures were confirmed by high-resolution transmission electron microscopy (HR-TEM; JEOL, Japan, 300 kV) and UV-vis spectroscopy (Agilent 8453 spectrophotometer, USA). FIG. 9B shows the HRTEM images of nanostructures obtained from reactions with different addition amounts of the precursor. The asymmetric Au growth on the surface of AuNPs was clearly observed in all images of FIG. 9B, but the size of snowman-like nanostructures increased as the addition amount of the precursor increased. The UV-vis data (FIG. 9C) show that the plasmonic peaks of the nanostructures were not greatly affected by varying the addition amount of the precursor, but the intensity of the peak increased as the addition amount of the precursor increased.

Figure 9C:
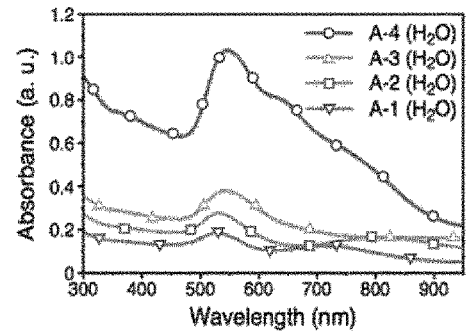
FIG. 9C shows UV-Vis spectra of Au—Au head-body nanoparticles by increasing addition amount of precursors.
Figure 9B:
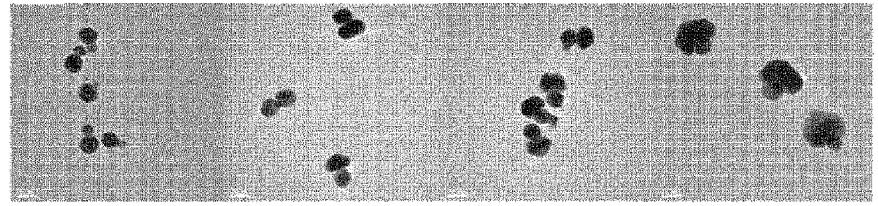
FIG. 9B shows HR-TEM images of Au—Au head-body nanoparticles by increasing additional amount of precursors.

Therefore, FIGS. 9B and 9C suggest that the size of snowman-like nanostructures increases, as the addition amount of the precursor increases.

EXAMPLE 12

Detectability of Nanoparticles Depending on their Size

In order to compare the detectability of nanoparticles depending on their size, surface enhanced Raman scattering (SERS) spectra of the Au—Au head-body nanoparticles with different sizes that were prepared in Examples 10 and 11 were measured. A Renishaw inVia Raman microscope equipped with 514 nm, 633 nm and 785 nm lasers was used for Raman measurement. This experiment was performed using a 633 nm laser with a power of 10 mW for acquisition time of 30 sec. The results are shown in FIG. 10.

Figure 10:
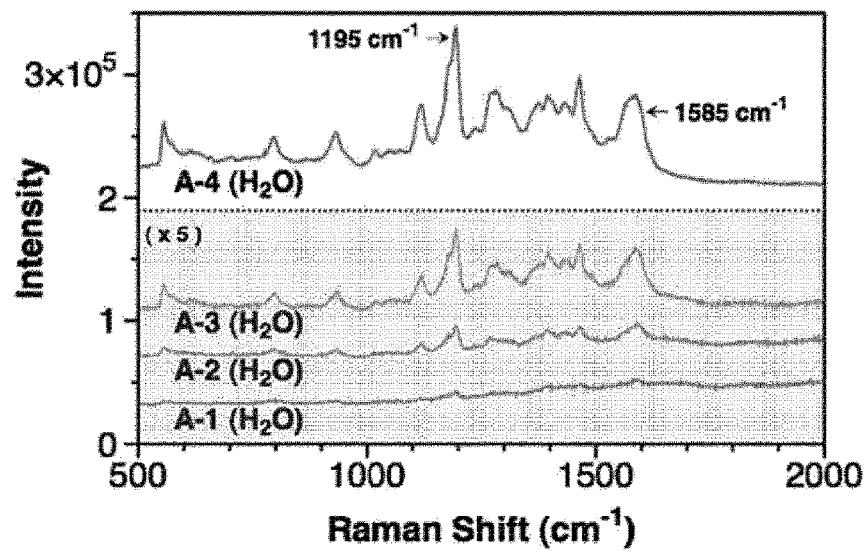
FIG. 10 shows Surface Enhanced Raman Scattering (SERS) spectra of Au—Au head-body nanoparticles with different sizes.
Figure 13A:
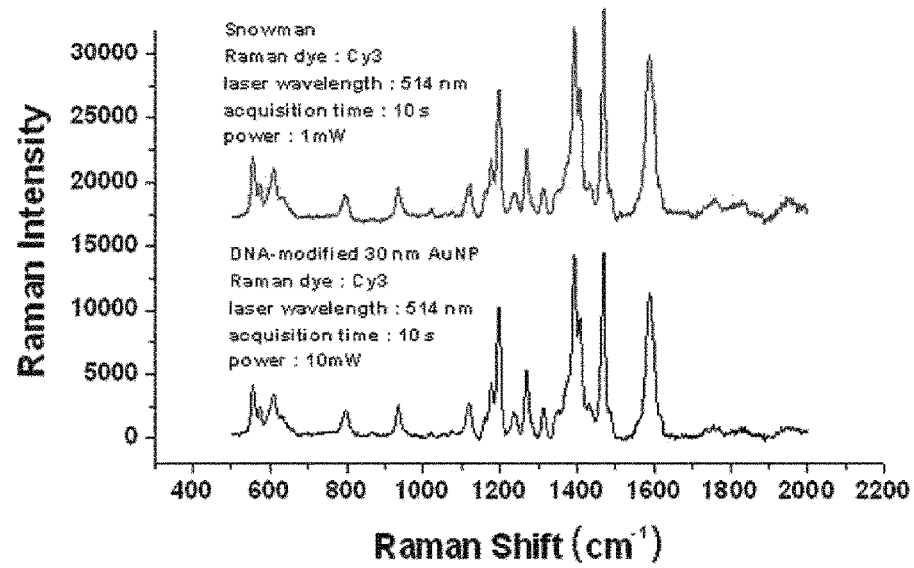
FIGS. 13A-13C, 14A-14C, 15A-15C and 16A-16C show Surface Enhanced Raman Scattering (SERS) spectra of Au—Ag head-body nanoparticle with the shape of nanosnowman.
Figure 13B:
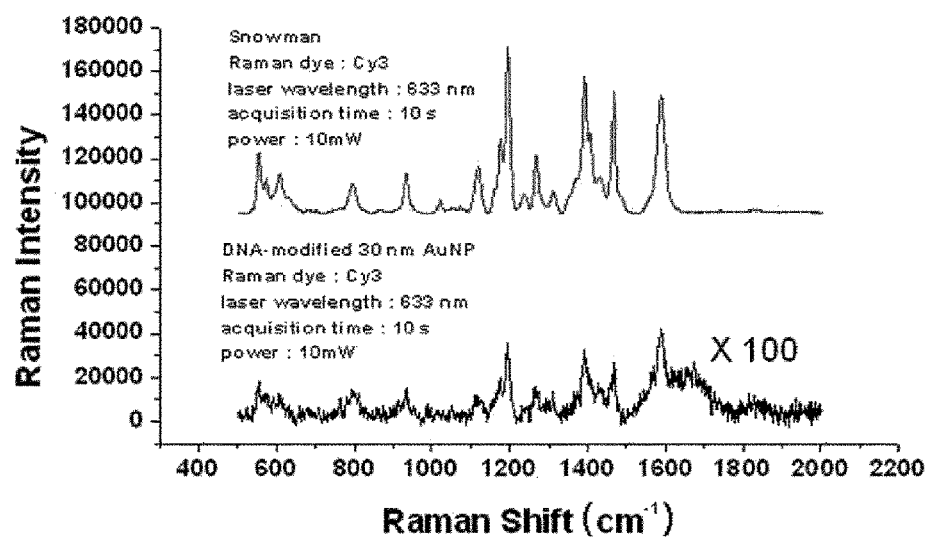
Figure 13C:
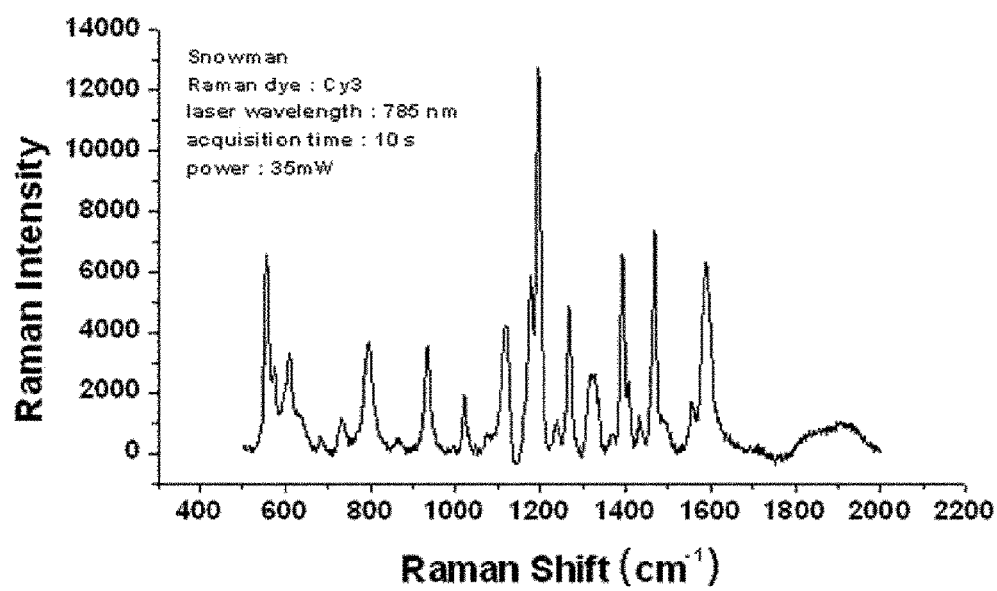
Figure 14A:
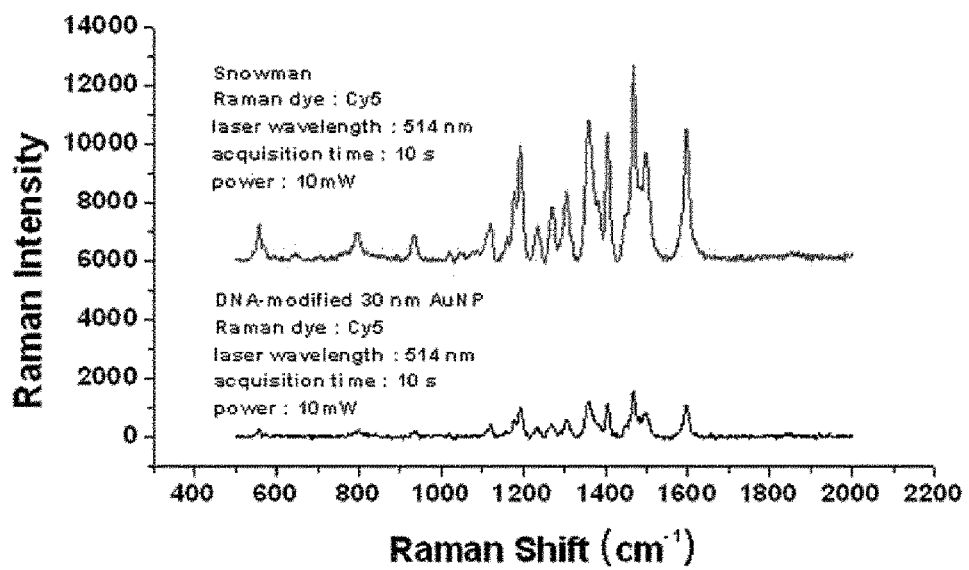
Figure 14B:
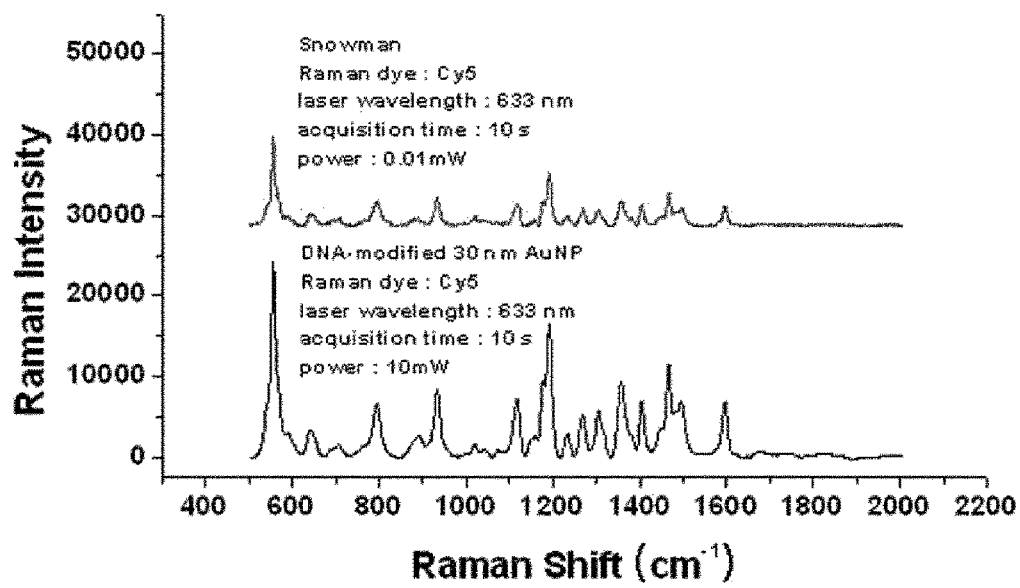
Figure 14C:
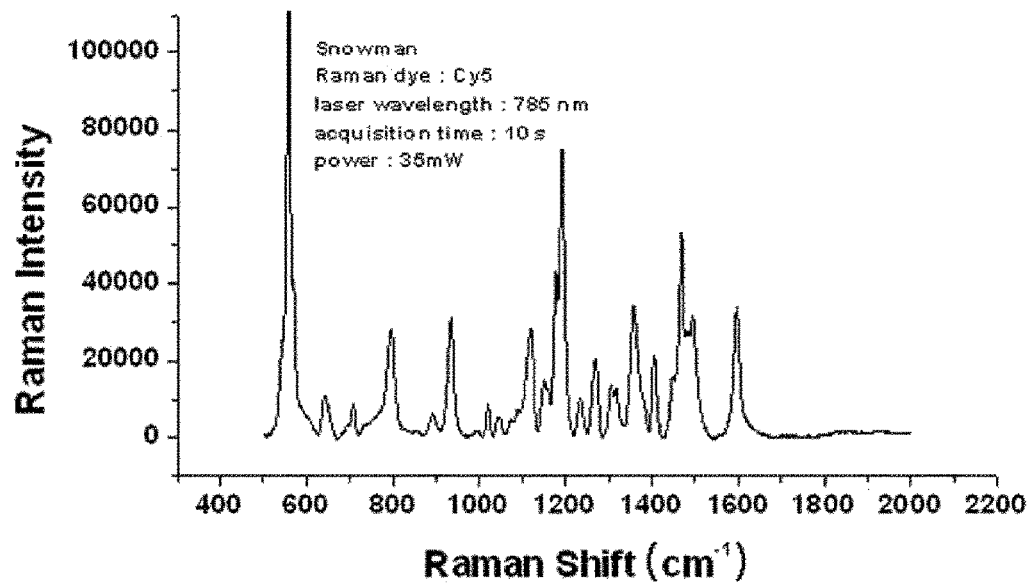
Figure 15A:
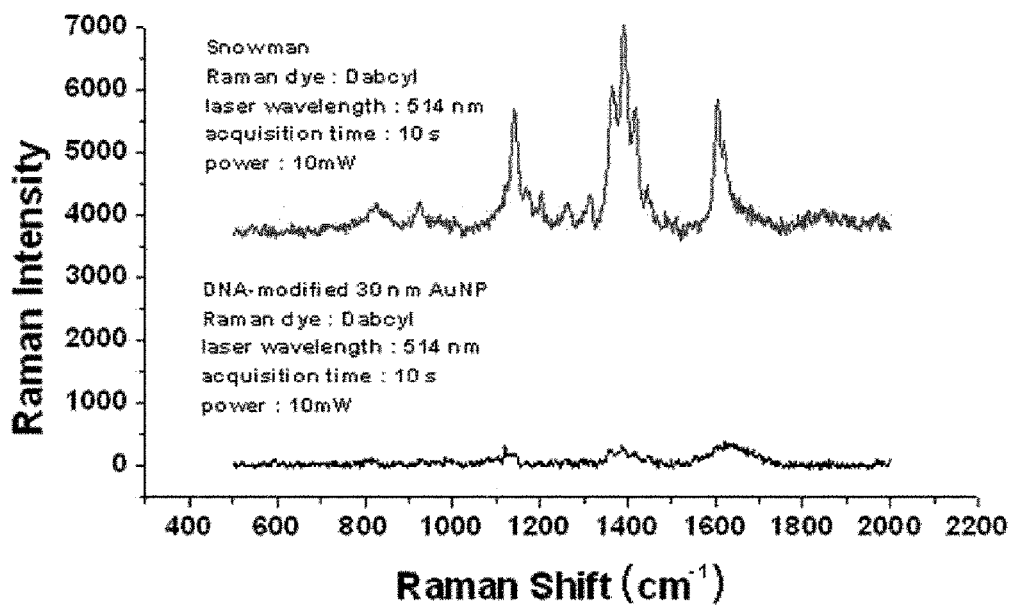
Figure 15B:
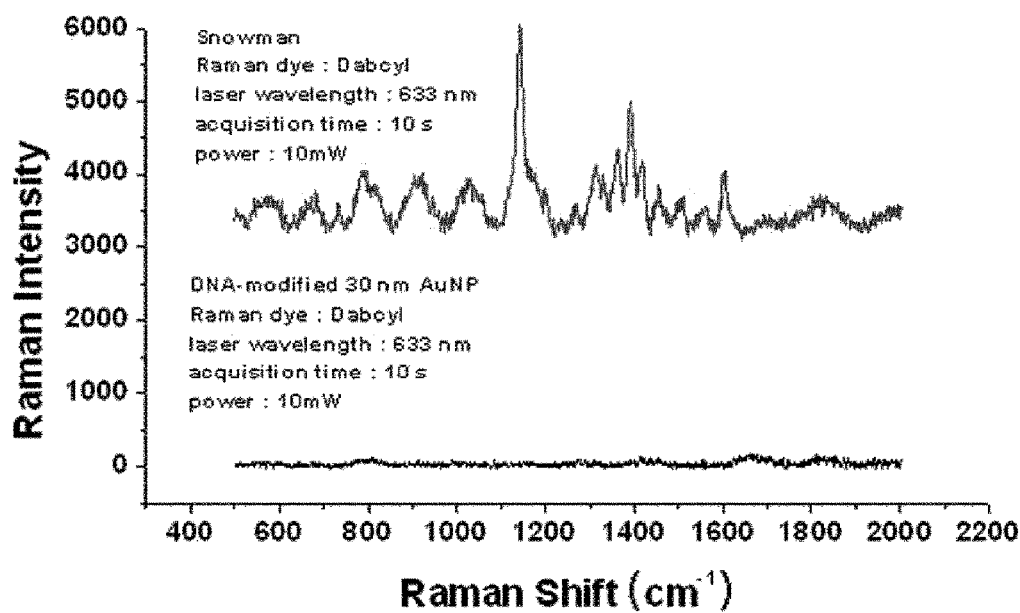
Figure 15C:
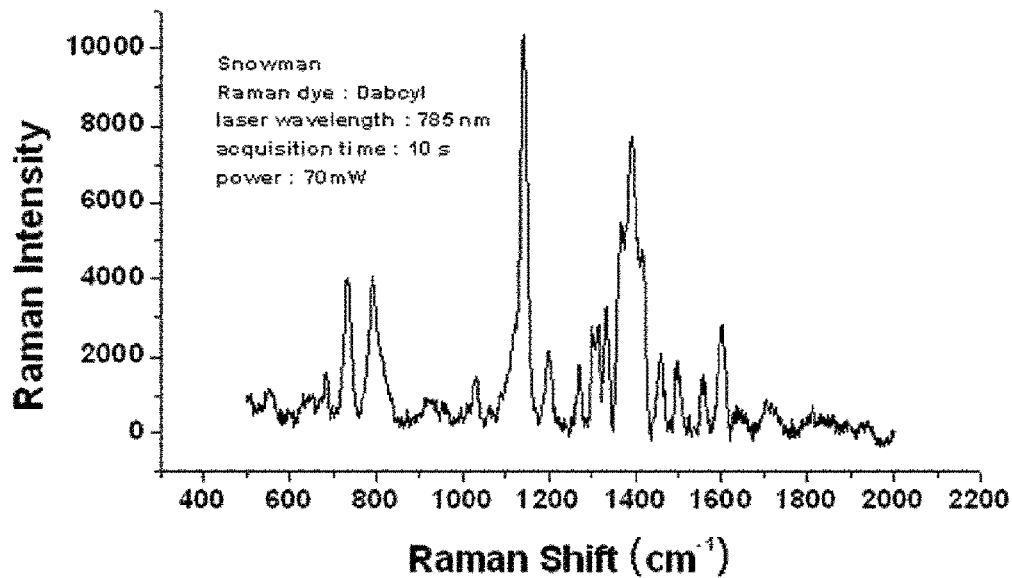
Figure 16A:
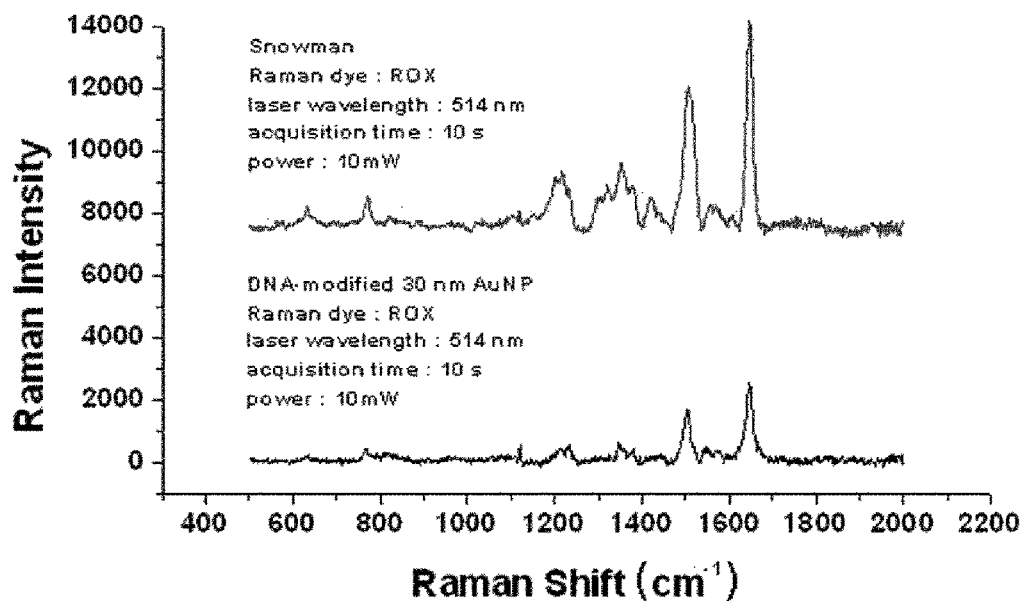
Figure 16B:
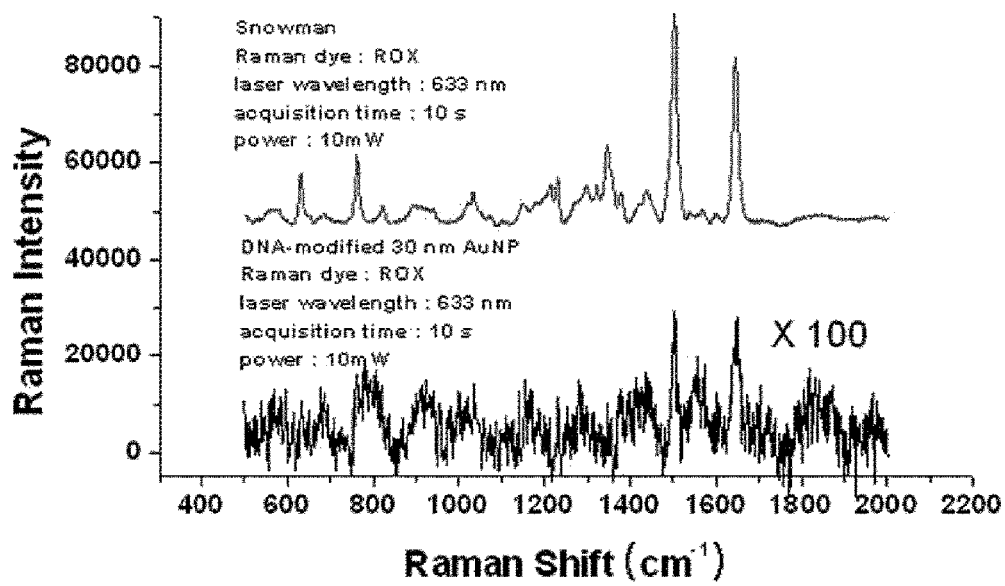
Figure 16C:
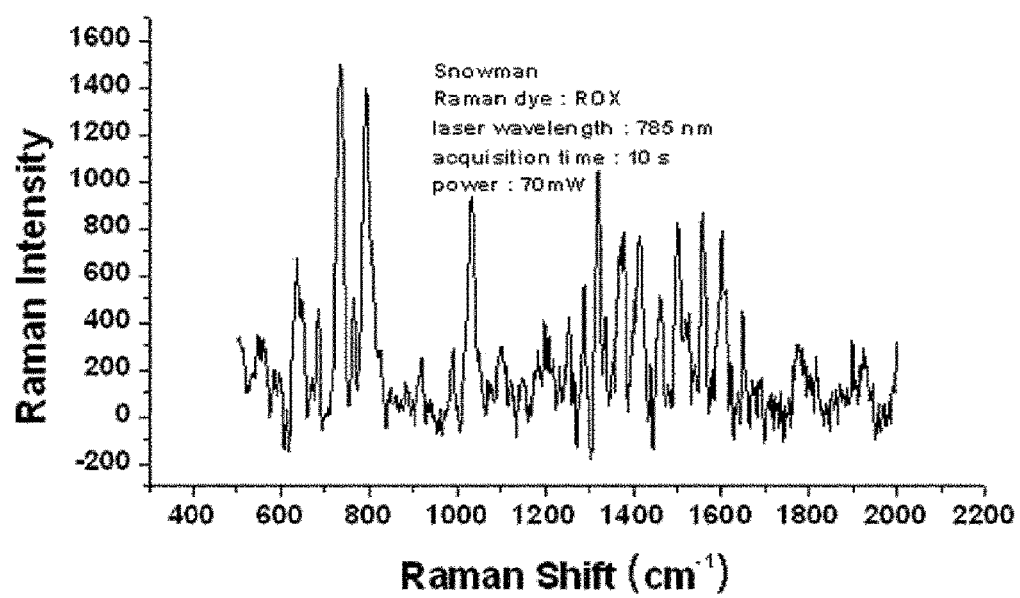

FIG. 10 shows that stronger SERS signals were observed, as the size of nanoparticles increased, suggesting that the detectability of nanoparticles can be improved by increasing their size.

EXAMPLE 13

Preparation of Ag—Ag Head-body Nanoparticles with the Shape of Nanosnowman

First, preparation was performed in the same manner as in Example 1, except for using DNA-AgNPs (40 nm silver nanoparticles) as seeds.

Next, the nanosnowman structures were synthesized by using the DNA-AgNPs as seeds and adding Ag precursors and other reagents to grow Ag structures on the DNA-AgNP surface.

Ag—Ag head-body nanosnowman structures were synthesized using 1% polyvinylpyrrolidone (PVP), 0.1 M (+)-sodium L ascorbate (L-SA) and 1 mM $AgNO_3$ in deionized water by a polymer-aided chemical reduction method. The PVP, L-SA and Ag precursors were added sequentially to the DNA-modified AgNP seed solution. The molar ratio between the reducing agent and $Ag^+$ (L-SA/Ag) was kept at 50 and the molar ratio between the number of PVP repeating units and $Ag^+$ (PVP/Ag) was kept at 30. Typically, 100 μL of 9.5 pM DNA-AgNP was reacted with 44.3 μL of 0.1 mM $AgNO_3$ solution in the presence of 14.8 μL of 0.1% PVP and 22.1 μL of 0.01 M L-SA at room temperature, respectively. The resulting mixture was mildly shaken in an orbital shaker. After reaction is finished, the solution was centrifuged at 8,000 rpm for 7 min to eliminate any un-reacted residues and then redispersed in deionized water.

The formed nanostructures were confirmed by high-resolution transmission electron microscopy (HR-TEM; JEOL, Japan, 300 kV) and UV-vis spectroscopy (Agilent 8453 spectrophotometer, USA), and the results are shown in FIGS. 11 and 12.

EXAMPLE 14

SERS Spectra of Au—Ag Head-body Nanoparticles with Shape of Nanosnowman

Au—Ag head-body nanoparticles with the shape of nanosnowman were prepared in the same manners as in Examples 1 and 2. For analysis of SERS spectra, Raman dye-modified oligonucleotides (DNA[5'-TAACAATAATC-COTC-$PEG_{18}$-$A_{10}$-(Cy3)-$(CH_2)_3$-SH-3'] (SEQ ID NO: 1), DNA [5'-TAACAATAATCCOTC-$PEG_{18}$-$A_{10}$-(Cy5)-(C$H_2)_3$-SH-3'] (SEQ ID NO: 1), DNA[5'-TAACAATAATC-COTC-$PEG_{18}$-$A_{10}$-(Dabcyl)-$(CH_2)_3$-SH-3'] (SEQ ID NO: 1), DNA[5'-TAACAATAATCCOTC-$PEG_{18}$-$A_{10}$-(ROX)-$(CH_2)_3$-SH-3']) (SEQ ID NO: 1) were used to prepare Au—Ag head-body nanoparticles with the shape of nanosnowman, and DNA-modified gold nanoparticles were prepared as a control.

A Renishaw inVia Raman microscope equipped with 514 nm, 633 nm and 785 nm lasers was used for Raman measurement. This experiment was performed under the conditions of a power of 10-70 mW and acquisition time of 10 sec. The results are shown in FIGS. 13A-13C, 14A-14C, 15A-15C and 16A-16C. As shown in FIGS. 13A-13C, 14A-14C, 15A-15C and 16A-16C, the nanosnowman-shaped nanoparticles showed remarkably increased SERS intensity, compared to the control gold nanoparticles.

EXAMPLE 15

Preparation of Au—Ag Head-body Nanoparticles with Shape of Nanosnowman using Various Nanoparticle Seeds First, DNA-AuNPs to be used as seeds were prepared in the same manner as in Example 1, except for using gold nanoparticles with the shape of nanorod (15 nm-50 nm), nanocube (45 nm) or sphere (30 nm).

Next, the Au—Ag head-body structures were synthesized by using the DNA-AuNPs as seeds and adding Ag precursors and other reagents to grow Ag structures with the shape of nanorod, nanocube or sphere on the DNA-AuNP surface.

In detail, Au—Ag head-body structures were synthesized using 1% polyvinylpyrrolidone (PVP), 0.1 M (+)-sodium L ascorbate (L-SA) or hydroxyl amine (HA) and 1 mM $AgNO_3$ in deionized water by a polymer-aided chemical reduction method. The PVP, L-SA and Ag precursors were added sequentially to the DNA-modified AgNP seed solution.

Typically, in order to form spherical Ag body structures on nanorods, 70 μL of 0.1 pM DNA-AuNP dispersed in a 0.1 mM salt (NaCl) solution was reacted with 23.8 μL of 1 mM $AgNO_3$ solution in the presence of 7.9 μL of 0.1% PVP and 11.9 μL of 0.1 M L-SA at room temperature, respectively. The molar ratio between the reducing agent and $Ag^+$ (L-SA/Ag) was kept at 50 and the molar ratio between the number of PVP repeating units and $Ag^+$ (PVP/Ag) was kept at 30. The resulting mixture was mildly shaken in an orbital shaker. After reaction is finished, the solution was centrifuged at 8,000 rpm for 7 min to eliminate any un-reacted residues and then redispersed in deionized water (FIG. 17). The formed nanostructures were confirmed by high-resolution transmission electron microscopy (TEM; JEOL, Japan, 200 kV), and the results are shown in FIG. 17.

Typically, in order to form spherical Ag body structures on nanocubes, 70 μL of 0.23 pM DNA-AuNP dispersed in a 0.003 M salt (NaCl) solution was reacted with 170.5 μL of 1 mM AgNO$_3$ solution in the presence of 57 μL of 1% PVP and 85 μL of 0.1 M L-SA at room temperature, respectively. The resulting mixture was mildly shaken in an orbital shaker. The molar ratio between the reducing agent and Ag$^+$ (L-SA/Ag) was kept at 50 and the molar ratio between the number of PVP repeating units and Ag$^+$ (PVP/Ag) was kept at 30. After reaction is finished, the solution was centrifuged at 8,000 rpm for 7 min to eliminate any un-reacted residues and then redispersed in deionized water (FIG. 18). The formed nanostructures were confirmed by high-resolution transmission electron microscopy (TEM; JEOL, Japan, 200 kV), and the results are shown in FIG. 18.

Typically, in order to form nanorod or nanocubic Ag body structures on spheres, 100 μL of 0.2 pM DNA-AuNP dispersed in a 0.003 M salt (NaCl) solution was reacted with 200 μL of 1 mM AgNO$_3$ solution in the presence of 4.45 μL of 1% PVP and 20 μL of 0.1 M L-SA at room temperature, respectively. The resulting mixture was mildly shaken in an orbital shaker. The molar ratio between the reducing agent and Ag$^+$ (L-SA/Ag) was kept at 10 and the molar ratio between the number of PVP repeating units and Ag$^+$ (PVP/Ag) was kept at 2. In particular, to form nanocubic Ag body structures, AgNO$_3$ precursors were added dropwise using a pump at a rate of 5 ml/hour. After reaction is finished, the solution was centrifuged at 8,000 rpm for 7 min to eliminate any un-reacted residues and then redispersed in deionized water (FIG. 19). The formed nanostructures were confirmed by high-resolution transmission electron microscopy (TEM; JEOL, Japan, 200 kV), and the results are shown in FIG. 19.

EXAMPLE 16

Preparation of Hollow Au Body Using Au—Ag Head-body Nanoparticles with Shape of Nanosnowman First, DNA-AuNPs to be used as seeds were prepared in the same manner as in Example 1, except for using spherical gold nanoparticles (30 nm).

Next, the Au—Ag head-body structures were synthesized by using the DNA-AuNPs as seeds and adding Ag precursors and other reagents to grow spherical Ag structures on the DNA-AuNP surface, in the same manner as in Example 13.

Next, the Au—Au head-body (hollow) structures were synthesized by using the Au—Ag head-body nanoparticles with the shape of nanosnowman as seeds and adding Au precursors and other reagents to form hollow Au body structures. After reaction is finished, the solution was centrifuged at 6,000 rpm for 7 min to eliminate any un-reacted residues and then redispersed in deionized water.

In detail, Au—Au head-body (hollow) structures were synthesized using 0.01 M cetyltrimethylammonium chloride (CTAC), and 0.05 mM Gold (III) chloride trihydrate (HAuCl$_4$·3H$_2$O) in deionized water by galvanic replacement. The CTAC and Au precursors were added sequentially to the seed solution of Au—Ag head-body nanoparticle with the shape of nanosnowman. Typically, 200 μL of 0.23 pM Au—Ag head-body nanoparticles with the shape of nanosnowman was reacted with 432 μL of Au precursor solution in the presence of 800 μL of 0.01 M CTAC at 80° C. To form hollow structures, Au precursors were added dropwise using a pump at a rate of 2.5 ml/hour. After reaction is finished, the solution was centrifuged at 5,000 rpm for 7 min to eliminate any un-reacted residues and then redispersed in deionized water (FIG. 20).

The formed nanostructures were confirmed by high-resolution transmission electron microscopy (TEM; JEOL, Japan, 200 kV), and the results are shown in FIG. 20.

In particular, the hollow nanoparticles absorb rather than scatter the incident light (absorbance=absorption+scattering), compared to non-hollow nanoparticles. This phenomenon can be a significant factor in photoacoustic imaging, etc., because nanoparticles absorb light and absorbed particles generate acoustic waves by local thermal expansion. Therefore, as absorption increases, the resulting acoustic effects increase. In addition, the nanoparticles prepared in the shape of head-body structure can be used as a complex imaging probe, because the effect of amplifying Raman signals can be improved as described above.

Effect of the Invention

The present invention provides nanoparticles in the shape of nanosnowman with head and body parts, which can offer platforms for DNA-based assembly of various aligned and unconventional nanostructures, is highly applicable to the detection of analytes such as DNA and proteins (biomarkers) associated with the onset and progression of a particular disease, and can be used in large-scale genome sequence analysis, single-nucleotide polymorphism (SNP) detection, base sequencing, gene fingerprinting, disease relationship, and drug development.

What is claimed is:

1. A method for preparing snowman-shaped nanoparticles, which comprises a gold or silver nanoparticle head part, a gold or silver nanoparticle body part, and a plurality of oligonucleotides bound to the surface of the head part, wherein a portion of the head part is located on a concave region in a portion of the body part, and a portion of the oligonucleotides bound to the surface of the head part are buried in the concave region in the body part, and the remaining portion of the oligonucleotides are exposed on the surface of the head part, comprising the following steps of:
1) modifying a gold or silver nanoparticle with oligonucleotides to form the head part (step 1); and
2) reacting the oligonucleotide-modified gold or silver nanoparticle with a gold or silver precursor in the presence of NaCl at a concentration of 1 nM to 0.1 M, a reducing agent, and a stabilizer to introduce a complex of the precursor and the stabilizer to the nanoparticle and induce a directional growth of a gold or silver nanostructure, and form the body part which buries a portion of the oligonucleotides bound to the surface of the head part in the concave region thereof (step 2).

2. The method according to claim 1, wherein the gold or silver precursor is AgNO3, AgClO4 or HAuCl4.

3. The method according to claim 1, wherein step 2) is performed under the condition of pH 2 to 7.

4. The method according to claim 1, wherein the reducing agent is hydroquinone, sodium borohydride (NaBH4), sodium ascorbate, hydroxyl amine or a combination thereof.

5. The method according to claim 1, wherein the stabilizer is a material containing nitrogen or oxygen having a lone pair of electrons.

6. The method according to claim 1, wherein the stabilizer is polyvinylpyrrolidone (PVP).

7. The method according to claim 1, wherein the head part and the body part are asymmetric in size.

8. The method according to claim 1, wherein a part of the oligonucleotides bound to the surface of the head part are exposed outside and the rest thereof are buried in a concave region in the upper portion of the body part, and consequently, the nanoparticle has asymmetrically modified oligonucleotides.

9. The method according to claim 1, wherein the oligonucleotides are bound to the surface of the gold or silver head part by any one functional group selected from the group consisting of a thiol group, an amino group, and an alcohol group.

10. The method according to claim 9, wherein the oligonucleotide includes a spacer sequence between the functional group and the oligonucleotide.

11. The method according to claim 10, wherein the spacer sequence is represented by $-PEG_x-Y_y-(CH2)_z-$, x is an integer of 0 to 30, y is an integer of 0 to 30, z is an integer of 3 to 6, and Y is adenine, thymine, guanine or cytosine, respectively.

12. The method according to claim 1, wherein a Raman active molecule is bound to the oligonucleotide.

* * * * *